US005602174A

United States Patent [19]

Maschler

[11] Patent Number: 5,602,174
[45] Date of Patent: Feb. 11, 1997

[54] TREATMENT

[75] Inventor: Harald Maschler, Gronau, Germany

[73] Assignee: Beecham Wuefling GmbH & Co., Munich, Germany

[21] Appl. No.: 458,046

[22] Filed: Jun. 1, 1995

Related U.S. Application Data

[62] Division of Ser. No. 845,522, Mar. 4, 1992, abandoned.

[30] Foreign Application Priority Data

Feb. 15, 1986 [GB] United Kingdom ............... 8603765 U

[51] Int. Cl.$^6$ .......................... A61K 31/27; C07C 271/44
[52] U.S. Cl. ...................... 514/478; 514/522; 514/561; 514/564; 514/821; 558/416; 560/27
[58] Field of Search .................. 564/367; 514/619, 514/620, 561, 564, 478, 522, 821; 560/27; 558/416

[56] References Cited

U.S. PATENT DOCUMENTS

| | | | |
|---|---|---|---|
| 2,670,374 | 2/1954 | Cusic et al. ............................. | 260/558 |
| 3,049,562 | 8/1962 | Wright et al. ........................... | 260/553 |
| 3,573,320 | 3/1971 | Jansen et al. ........................... | 260/305 |
| 3,789,073 | 1/1974 | Narayanan et al. ..................... | 260/558 |
| 4,322,434 | 3/1982 | Neustadt et al. ........................ | 424/304 |
| 4,562,201 | 12/1985 | Stout et al. ............................... | 514/422 |
| 4,657,929 | 4/1987 | Ince et al. ................................ | 514/524 |
| 5,079,248 | 1/1992 | Cross et al. ............................. | 514/237.5 |

FOREIGN PATENT DOCUMENTS

| | | |
|---|---|---|
| 667899 | 7/1963 | Canada . |
| 1191846 | 8/1985 | Canada . |
| 247345 | 12/1987 | European Pat. Off. . |
| 1118212 | 3/1958 | Germany . |
| 1170961 | 5/1964 | Germany . |
| 3242344 | 5/1984 | Germany . |
| 3428526 | 2/1986 | Germany . |
| 862467 | 3/1961 | Great Britain . |
| 1004071 | 9/1965 | Great Britain . |
| 3028137 | 3/1978 | Japan . |
| 1033256 | 6/1966 | United Kingdom . |
| 1050132 | 12/1966 | United Kingdom . |

OTHER PUBLICATIONS

Chemical Abstracts, vol. 77, No. 7, Aug. 14, 1972 p. 505, Columbus Ohio, US. (619672).

Chemical Abstracts, vo. 87, No. 19, Nov. 7, 1977, p. 14, Abstract #145548.

*Primary Examiner*—Shailendra Kumar
*Attorney, Agent, or Firm*—Stephen Venetianer; Edward T. Lentz

[57] ABSTRACT

A method of treatment or prophylaxis of angina in mammals, such as humans, which comprises the administration to the sufferer of an effective amount of a compound of formula (I), or a pharmaceutically acceptable salt thereof, or a solvate of any of the foregoing:

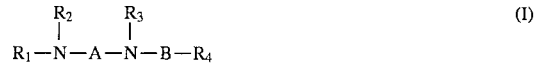

wherein $R_1$, $R_2$, $R_3$, $R_4$, A and B are herein defined.

3 Claims, No Drawings

TREATMENT

CROSS-REFERENCE

This is a division of Ser. No. 845,522 filed Mar. 4, 1992, now abandoned.

The present invention relates to a method of treatment or prophylaxis of angina in mammals, and to novel compounds useful in such a method.

British Patent 862467 discloses a class of compounds of formula (A):

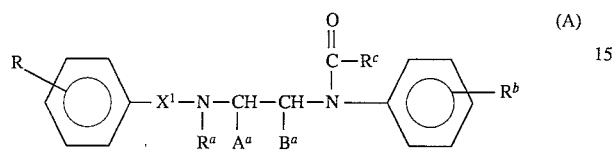

in which R is hydrogen or halogen or a lower alkoxy, hydroxy, lower alkanoyloxy, lower alkyl, nitro, amino or lower alkanoylamino radical, $R^b$ is hydrogen or halogen or a lower alkyl, lower alkoxy, hydroxy or lower alkanoyloxy radical, $R^a$ and $R^c$ are lower alkyl radicals, $X^1$ is a divalent hydrocarbon radical of 1–4 carbon atoms, and wherein said lower radicals contain not more than six carbon atoms, and where $A^a$ and $B^a$ can each be a hydrogen atom, a methyl group or ethyl group with the proviso that together they may not contain more than two carbon atoms, and acid addition slats thereof. The compounds are described as active as analgesics. Compounds specifically disclosed in the patent include those where [R, $X^1$, $R^a$, $A^a$, $B^a$, $R^c$, $R^b$] take the following combination of values:

[H, $CH_2$, $CH_3$, H, H, $nC_3H_7$, H], [H, $CH_2$, $CH_3$, H, H, $iC_3H_7$, H], [H, $(CH_2)_2$, $CH_3$, H, $CH_3$, $nC_3H_7$, H], [H, $(CH_2)_2$, $CH_3$, $CH_3$, H, $nC_3H_7$, $H_3$, [H, $(CH_2)_2$, $CH_3$, $CH_3$, H, $iC_3H_7$, H] and [H, $(CH_2)_2$, $CH_3$, $CH_3$, H, $nC_4H_9$, H].

In European Journal of Pharmacology, 44(1977) 251–270, Frans G. Van den Brink and Erik J. Lien, a group of compounds are studied in a histaminic and a cholinergic system. The compounds are of formula (B):

where the variables [$R^d$, $R^e$, $A^b$, $R^f$, $B^b$, $R^g$] take the following values:
[phenyl, benzyl, $(CH_2)_2$, H, $(CH_2)_2$, phenyl]
[phenyl, benzyl, $(CH_2)_2$, $CH_3$, $CH_2$, phenyl]
[phenyl, benzyl, $(CH_2)_2$, $CH_3$, $(CH_2)_2$, phenyl]
[phenyl, benzyl, $(CH_2)_2$, $CH_3$, $(CH_2)_3$, phenyl]
[4-chlorophenyl, benzyl, $(CH_2)_2$, H, $(CH_2)_2$, phenyl]
[4-chlorophenyl, benzyl, $(CH_2)_2$, $CH_3$, $(CH_2)_2$, phenyl]
[phenyl, 4-chlorobenzyl, $(CH_2)_2$, $CH_3$, $(CH_2)_2$, phenyl]
[phenyl, benzyl, $(CH_2)_2$, $CH_3$, $(CH_2)_2$, 4-chlorophenyl]
In Ann. Ist. Super. Sanita 1971, 7 (Pt. 4), 533–9, the compounds

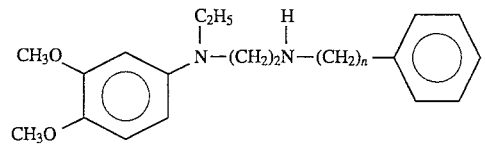

where n is 1 or 2, are described as chemical intermediates in the preparation of certain benzodiazepines.

It has been discovered that compounds of formula (I) and pharmaceutical salts thereof:

wherein $R_1$ ana $R_4$ are independently phenyl optionally substituted by one, two or three of halogen, trifluoromethyl, $C_{1-4}$ alkoxy, $C_{1-4}$ alkyl, cyano, hydroxy, nitro, $NR_5R_6$ or $O_2SNR_5R_6$ wherein $R_5$ and $R_6$ are independently hydrogen or $C_{1-6}$ alkyl or together are $C_{3-6}$ polymethylene, or disubstituted at adjacent carbon atoms by $C_{1-2}$ alkylenedioxy and optionally further substituted by one of the above groups;

$R_2$ is selected from $(CH_2)_z$ CN where z is O or an integer from 1 to 4, $C_{1-12}$ alkyl, $C_{3-7}$ cycloalkyl, $C_{3-7}$ cycloalkyl $C_{1-4}$ alkyl, phenyl $C_{1-4}$ alkyl, pyridyl, pyridyl $C_{1-4}$ alkyl, $COR_7$, $COCH_2COR_7$, $SO_2R_7$, $CO_2R_7$, $CONHR_7$ and $CSNHR_7$, where $R_7$ is selected from $C_{3-12}$ alkyl, $C_{3-7}$ cycloalkyl, $C_{3-7}$ cycloalkyl $C_{1-4}$ alkyl, phenyl and phenyl $C_{1-4}$ alkyl, any alkyl moiety in $R_7$ optionally substituted by hydroxy or $C_{1-4}$ alkanoyloxy, any pyridyl or phenyl moiety in $R_2$ optionally substituted as defined for $R_1$ and $R_4$ and any cycloalkyl moiety in $R_2$ optionally substituted by one or two $C_{1-4}$ alkyl groups;

$R_3$ is hydrogen or $C_{1-4}$ alkyl;

A represents $C_{2-5}$ alkylene; and

B represents $C_{1-4}$ alkylene, have been found to possess cardiovascular activity, in particular calcium antagonistic activity which indicates that they are of potential use in the treatment of angina.

Accordingly, the invention provides a method of treatment or prophylaxis of angina in mammals, such as humans, which comprises the administration of an effective amount of a compound of formula (I), or a pharmaceutically acceptable salt thereof, or a solvate of any of the foregoing, to the sufferer.

An amount effective to treat the disorder hereinbefore described depends on the relative efficacies of the compounds of the formula (I), the nature and severity of the disorders being treated and the weight of the mammal. However, a unit dose will normally contain 0.1 to 500 mg for example 2 to 50 mg, of the compound of the invention. Unit doses will normally be administered once or more than once a day, for example 2,3,4,5 or 6 timer a day, more usually 2 to 4 times a day, such that the total daily dose is normally in the range, for a 70 kg adult of 0.1 to 2500 mg, more usually 50 to 2000 mg, for example 10 to 75 mg, that is in the range of approximately 0.002 to 35 mg/kg/day, more usually 1 to 30 mg/kg/day, for example 0.15 to 1 mg/kg/day.

At the above described dosage range, no toxicological effects are indicated for the compounds of the invention.

In such treatment, the compound may be administered by any suitable route, e.g. by the oral, parenteral or topical routes. For such use, the compound will normally be employed in the form of a pharmaceutical composition in association with a human or veterinary pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol, preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the compound and may be prepared in a conventional manner, for example, as described in the standard textbooks such as 'Dermatological Formulations'—S. W. Barry (Drugs and the Pharmaceutical Sciences—Dekker) or Harrys Cosmeticology (Leonard Hill Books).

In addition such compositions may contain further active agents such as anti-hypertensive agents and diuretics.

As is common practice, the compositions will usually be accompanied by written or printed directions for use in the medical treatment concerned.

The invention also provides the use of a compound of formula (I) or a pharmaceutically acceptable salt thereof, or a solvate of any of the foregoing, for the preparation of a medicament for the treatment or prophylaxis of angina in mammals.

The invention further provides a pharmaceutical composition for use in the treatment or prophylaxis of angina in mammals, which comprises a compound of formula (I) or a pharmaceutically acceptable salt thereof, or a solvate of any of the foregoing, and a pharmaceutically acceptable carrier.

Such compositions may be prepared in the manner hereinbefore described.

In formula (I), it is understood that alkyl and alkylene includes straight- and branched-chain alkyl and alkylene.

Suitable values for $R_1$ and $R_4$ include phenyl, phenyl di-substituted by methylenedioxy and optionally further substituted by chloro, or phenyl substituted by one, two or three of fluoro, chloro, bromo, trifluoromethyl, methoxy, ethoxy, n- or iso-propoxy, methyl, ethyl, n- or iso-propyl, cyano, hydroxy or amino optionally substituted by one or two methyl groups. $R_1$ and $R_4$ are preferably the same group, most preferably 3,4-dimethoxyphenyl.

Suitable values for phenyl moieties in $R_2$ include phenyl, 2-, 3- and 4-nitrophenyl, 3,5-dinitrophenyl, 3-methoxyphenyl, 3-methoxy-6-methylphenyl, 2-trifluoromethylphenyl, 2,4,6-trimethylphenyl, 2,6-dichlorophenyl, 2-chloro-3,4-methylenedioxyphenyl, 4-cyanophenyl, 4-chlorophenyl and 4-methylphenyl.

Suitable values for cycloalkyl moieties in $R_2$ include cyclopentyl, cyclohexyl and menthyl.

Suitable values for alkylene moieties in $R_2$ include —$CH_2$—, —$CH(CH_3)$— —$CH_2CH_2CH_2$— and —$CH_2CH_2$—. Suitable values for $R_2$ when alkyl include n-pentyl. Alkyl $R_7$ in $R_2$ may be $C_{4-12}$, more preferably $C_{5-12}$ alkyl groups which are preferably straight-chain. Suitable values for alkyl $R_7$ in $R_2$ includes n- and iso- $C_3H_7$, n-$C_4H_9$, n-$C_5H_{11}$, n$C_6H_{13}$, n$C_7H_{15}$, n$C_8H_{17}$ and n$C_{11}H_{23}$.

Suitable values for pyridyl moieties in $R_2$ include 2-pyridyl optionally 3,5-dinitro-substituted.

Suitable values for optional substituents on alkyl moieties in $R_7$ include acetoxy.

Suitable values for z in $R_2$ include 0 or 1.

Suitable values for $C_{1-4}$ alkyl groups in $R_2$ include methyl and ethyl.

Suitable values for $R_3$ include hydrogen, methyl, ethyl, n- and iso-propyl, and n, iso-, sec- and t-butyl. Preferably $R_3$ is methyl.

Suitable values for A and S include —$(CH_2)_2$— and —$(CH_2)_3$—.

There is a sub-group of compounds within formula (I) of formula (II):

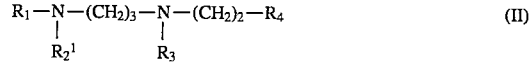

(II)

wherein:

$R_1$, $R_3$ and $R_4$ are as defined in formula (I); and $R_2^1$ is $(CH_2)_zCN$, $C_{1-12}$ alkyl, $C_{3-7}$ cycloalkyl, $C_{3-7}$ cycloalkyl $C_{1-4}$ alkyl or phenyl $C_{1-4}$ alkyl wherein z is as defined in formula (I) and any phenyl, alkyl, or cycloalkyl moieties in $R_2^1$ are optionally substituted as defined for corresponding variables $R_2$ in formula (I).

Suitable and preferred values for $R_2^1$, $R_1$, $R_3$ and $R_4$ are as described for the corresponding variables under formula (I).

A preferred value for $R_1$ and $R_4$ is 3,4-dimethoxyphenyl.

There is another group of compounds within formula (I) of formula (IIa):

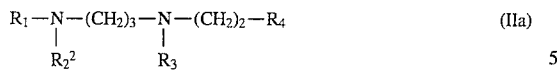

wherein $R_2^2$ is $COR_7$ where $R_7$ is as defined in formula (I), and the remaining variables are as defined in formula (I).

There is further group of compounds within formula (I) of formula (IIb):

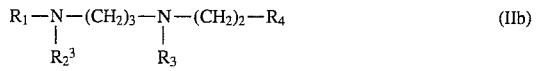

wherein $R_2^3$ is $CO_2R_7$ or $SO_2R_7$ where $R_7$ is as defined in formula (I), and the remaining variables are as defined in formula (I).

There is another group of compounds within formula (I) of formula (IIc):

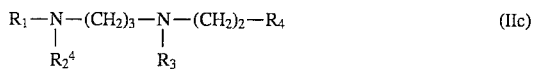

wherein $R_2^4$ is $CONHR_7$ or $CSNHR_7$ where $R_7$ is as defined in formula (I), and the remaining variables are as defined in formula (I).

Suitable and preferred values for the variables of formulae (IIa), (IIb) and (IIc) are as described for the corresponding variables under formula (II).

It will of course be realised that the compounds of formula (I) possess two chiral centres and therefore exist in more than one stereoisomeric form. The invention extends to any of the stereoisometric forms, including enantiomers of the compounds of formula (I) and to mixtures thereof, including racemates. The different stereoisomeric forms may be separated or resolved one from the other by the usual methods or any given isomer may be obtained by stereospecific or asymmetric syntheses.

The pharmaceutically acceptable salts of the compounds of formula (I) include acid addition salts with conventional acids such as hydrochloric, hydrobromic, boric, phosphoric, sulphuric and pharmaceutically acceptable organic acids such as acetic, tartaric, maleic, citric, succinic, benzoic, ascorbic, methanesulphonic, α-keto-glutaric, α-glycerophosphoric, and glucose-1-phosphoric acids. Preferably the acid addition salt is a hydrochloride.

Pharmaceutically acceptable salts also include quaternary salts. Examples of quaternary salts include such compounds quaternised by compounds such as $R_8$-T wherein $R_8$ is $C_{1-6}$ alkyl, phenyl-$C_{1-6}$ alkyl or $C_{5-7}$ cycloalkyl, and T is a radical corresponding to an anion of an acid. Suitable examples of $R_8$ include methyl, ethyl and n- and iso-propyl; and benzyl and phenethyl. Suitable T include halide such as chloride, bromide and iodide.

Pharmaceutically acceptable salts also include pharmaceutically acceptable N-oxides, and the invention extends to these.

The compounds of the formula (I) and their pharmaceutically acceptable salts may also form solvates with pharmaceutically acceptable solvates and the invention extends to these.

It will also be realised that salts of the compounds of the formula (I) which are not pharmaceutically acceptable may be useful as intermediates in the preparation of pharmaceutically acceptable salts of compounds of the formula (I) or the compounds of the formula (I) themselves, and as such form an aspect of the present invention.

The invention further provides a compound of formula (I) or a pharmaceutically acceptable salt thereof, or a solvate of any of the foregoing, with the proviso that the variables [$R_1$, $R_2$, A, $R_3$, B, $R_4$] do not take the following combinations of values:

[phenyl, $CO_nC_3H_7$, $(CH_2)_2$, $CH_3$, $CH_2$, phenyl]
[phenyl, $COiC_3H_7$, $(CH_2)_2$, $CH_3$, $CH_2$, phenyl]
[phenyl, $COnC_3H_7$, $CH(CH_3)CH_2$, $CH_3$, $(CH_2)_2$, phenyl]
[phenyl, $COnC_3H_7$, $CH_2CH(CH_3)$, $CH_3$, $(CH_2)_2$, phenyl]
[phenyl, $COiC_3H_7$, $CH_2CH(CH_3)$, $CH_3$, $(CH_2)_2$, phenyl]
[phenyl, $COnC_4H_9$, $CH_2CH(CH_3)$, $CH_3$, $(CH_2)_2$, phenyl]
[phenyl, benzyl, $(CH_2)_2$, H, $(CH_2)_2$, phenyl]
[phenyl, benzyl, $(CH_2)_2$, $CH_3$, $CH_2$, phenyl]
[phenyl, benzyl, $(CH_2)_2$, $CH_3$, $(CH_2)_2$, phenyl]
[phenyl, benzyl, $(CH_2)_2$, $CH_3$, $(CH_2)_3$, phenyl]
[4-chlorophenyl, benzyl, $(CH_2)_2$, H, $(CH_2)_2$, phenyl]
[4-chlorophenyl, benzyl, $(CH_2)_2$, $CH_3$, $(CH_2)_2$, phenyl]
[phenyl, 4-chlorobenzyl, $(CH_2)_2$, $CH_3$, $(CH_2)_2$, phenyl]
[phenyl, benzyl, $(CH_2)_2$, $CH_3$, $(CH_2)_2$, 4-chlorophenyl]

for use as an active therapeutic substance, and particularly for the treatment or prophylaxis of angina.

The class of compounds as just defined will be referred to hereinafter as compounds of formula (IA).

The invention also provides a pharmaceutical composition comprising a compound of formula (IA) and a pharmaceutically acceptable carrier.

In another aspect the invention provides a compound of formula (IA) with the proviso that the variables [$R_1$, $R_2$, A, $R_3$, B, $R_4$] do not take the following combinations of values:

[3,4-dimethoxyphenyl, $C_2H_5$, $(CH_2)_2$, H, $(CH_2)_2$, phenyl]
[3,4-dimethoxyphenyl, $C_2H_5$, $(CH_2)_2$, H, $CH_2$, phenyl]

The class of compounds as just defined will be referred to hereinafter as compounds of formula (IB).

Suitable and preferred values for variables in formula (IB) are as defined for the corresponding variables in formula (I).

In one sub-group of the formula (IB), $R_1$ and $R_4$ are independently phenyl substituted as defined in formula (I).

In another sub-group of the formula (IB), $R_2$ is $COR_7$ where $R_7$ is phenyl or phenyl $C_{1-4}$ alkyl, the phenyl moiety optionally substituted as defined for $R_1$ and $R_4$.

In a further subgroup of formula (IB), $R_2$ is $C_{3-12}$ alkyl.

In another subgroup of formula (IB), $R_1$ and $R_4$ are independently phenyl substituted by one, two or three of halogen, trifluoromethyl, $C_{1-4}$ alkoxy, $C_{1-4}$ alkyl, cyano, hydroxy, nitro, $NR_5R_6$ or $O_2SNR_5R_6$ wherein $R_5$ and $R_6$ are independently hydrogen or $C_{1-6}$ alkyl or together are $C_{3-6}$ polymethylene, or aisubstituted at adjacent carbon atoms by $C_{1-2}$ alkylenedioxy;

$R_2$ is selected from $(CH_2)_z$ CN where z is O or an integer from 1 to 4, $C_{1-12}$ alkyl, $C_{3-7}$ cycloalkyl, $C_{3-7}$ cycloalkyl $C_{1-4}$ alkyl, phenyl $C_{1-4}$ alkyl, $COR_7$, $SO_2R_7$, $CO_2R_7$, $CONHR_7$ and $CSNHR_7$, where $R_7$ is selected from $C_{3-12}$ alkyl, $C_{3-7}$ cycloalkyl, $C_{3-7}$ cycloalkyl $C_{1-4}$ alkyl, phenyl and phenyl $C_{1-4}$ alkyl, any phenyl moiety in $R_2$ optionally substituted as defined for $R_1$ and $R_4$;

$R_3$ is hydrogen or $C_{1-4}$ alkyl;

A represents $C_{2-5}$ alkylene; and

B represents $C_{1-4}$ alkylene.

A process for the preparation of a compound of formula (I) or a pharmaceutically acceptable salt thereof comprises reacting together $R_{10}X$ and $YR_{11}$ wherein one of X and Y is a leaving group or aldehyde or ketone function and the other is a nitrogen nucleophile, the nitrogen nucleophile, $R_{10}$ and $R_{11}$, and the aldehyde or ketone function when present, being such that a compound of formula (III) is formed:

in which $R_2'$, $A'$, $R_3'$ and $B'$ are $R_2$, $A$, $R_3$ and $B$ respectively or groups convertible thereto, and thereafter, optionally or as necessary, converting $R_2'$, $A'$, $R_3'$, and/or $B'$ to $R_2$, $A$, $R_3$ and/or $B$, interconverting $R_2$ and/or $R_3$ and/or forming a pharmaceutically acceptable salt.

Suitable examples of $R_2'$ convertible to $R_2$ include hydrogen and $C_{1-3}$ alkanoyl. $R_2'$ $C_{1-3}$ alkanoyl may be converted to $R_2$ $C_{1-3}$ alkyl by reduction under conventional conditions, for example with $LiAlH_4$ as the reducing agent in an inert solvent such as tetrahydrofuran. $R_2'$ hydrogen may be converted to $R_2$ by conventional amine alkylation or acylation.

In a preferred embodiment the process comprises reacting a compound of formula (IIIa):

$$R_1-NH-A-NR_3'-B-R_4 \quad \text{(IIIa)}$$

wherein the variables are as defined in formula (III), (a) with a compound of formula (IV):

$$L-R_2' \quad \text{(IV)}$$

wherein $R_2'$ is $R_2$ as defined in formula (I) or a group convertible thereto, and L is a leaving group;

(b) with a compound of formula (V):

$$X^1=C=N-R_7 \quad \text{(V)}$$

wherein $X^1$ is O or S and $R_7$ is as defined in formula (I); or (c) with a compound of formula (VI):

(VI)

wherein $R_{12}$ and $R_{13}$ are such that

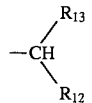

is $R_2$ as defined in formula (I) and thereafter, optionally or as necessary, converting $R_3'$ when a protecting group to $R_3$ and/or converting $R_3$ when hydrogen to another $R_3$ and/or converting $R_2'$ to $R_2$ and/or converting $R_2$ to other $R_2$ and/or forming a pharmaceutically acceptable salt.

In the compound of formula (IV), the leaving group L is a group readily displaceable by a nucleophile. Suitable examples of L are hydroxy, halogen such as chloro, bromo and iodo and acyloxy such as mesyloxy, tosyloxy, triflate, $C_{1-4}$ alkanoyloxy, $C_{1-4}$ alkoxycarbonyloxy and activated hydrocarbyloxy such as pentachlorophenoxy.

If the leaving group is hydroxy, then the reaction is preferably carried out in an inert non-hydroxylic solvent, such as benzene, toluene or diethyl ether in the presence of a dehydrating catalyst, such as a carbodiimide, for example dicyclohexylcarbodiimide. The reaction may be carried out at a non-extreme temperature such as $-10°$ to $100°$ C., for example $0°$ to $80°$ C.

If the leaving group is a halide, then the reaction is preferably carried out at a non-extreme temperature in an inert non-hydroxylic solvent, such as trichloromethane, xylene, benzene, toluene or diethyl ether. It is also preferably carried out in the presence of an acid acceptor, such as an organic base, in particular a tertiary amine, such as triethylamine, trimethylamine, pyridine or picoline, some of which can also function as a solvent. Alternatively, the acid acceptor can be inorganic, such as calcium carbonate, sodium carbonate or potassium carbonate.

If the leaving group is acyloxy, then the reaction is preferably carried in substantially the same manner as if the leaving group were hydroxy. Suitable examples of acyloxy leaving groups include $C_{1-4}$ alkanoyloxy, mesyloxy, tosyloxy and triflate.

If the leaving group is $C_{1-4}$ alkoxycarbonyloxy, then the reaction is preferably carried out in an inert solvent, such as methylenechloride, at a non-extreme temperature in the presence of an acid acceptor, such as triethylamine.

If the leaving group is activated hydrocarbonyloxy then the reaction is preferably carried out in an inert polar solvent, such as dimethylformamide. It is also preferred that the activated hydrocarbyloxy group is a pentachlorophenyl ester and that the reaction is carried out at ambient temperature.

When $R_2$ is an alkyl-type moiety, the leaving group is preferably halide or tosyloxy. When $R_2$ is an acyl-type moiety, the leaving group is preferably halide or hydroxy, more preferably halide.

The reaction between the compounds of formulae (IIIa) and (V) may be carried out under conditions suitable for the preparation of a urea, for example in an inert solvent such as chloroform at moderate temperature, suitably the boiling point of the solvent, for example $40°-80°$ C.

The reaction between the compounds of formulae (IIIa) and (VI) may be carried out under conditions suitable for a reductive alkylation, in the presence of a suitable reducing agent such as $NaCNBH_3$ in an inert solvent such as methanol.

Examples of N-protecting groups for $R_3'$ include $C_{1-6}$ alkanoyl, for example acetyl, propionyl, n- and iso-butyryl and 2,2-dimethylpropanoyl, benzoyl or benzyl optionally substituted in the phenyl ring by one or two substituents selected from $C_{1-4}$ alkyl, $C_{1-4}$ alkoxy, trifluoromethyl, halogen or nitro; and $C_{1-4}$ alkoxycarbonyl, for example tert-butoxycarbonyl.

Conversion of protected amino to amino may be effected conventionally.

When the protecting group is $C_{1-6}$ alkanoyl or optionally substituted benzoyl as defined, conversion to amino is conveniently effected by conventional base hydrolysis.

When the protecting group is $C_{1-4}$ alkoxycarbonyl or optionally substituted benzyl as defined, conversion to amino may be carried out conventionally, for example by hydrogenolysis. Suitable reactions are conventionally transition-metal catalysed hydrogenation, using for example palladium- or platinum-charcoal, at atmospheric pressure or a light excess thereover. A dry, inert, polar solvent such as dry ethanol and ambient temperatures are apt.

Subsequent conversion of $R_3$ when hydrogen to other $R_3$ may be carried out by conventional amine alkylation, for example with the appropriate aldehyde or ketone in a solvent such as acetonitrile or methanol, in the presence of a reducing agent such as an alkaline borohydride e.g. sodium cyanoborohydride.

Alternatively, conversion of an $R_3'$ $C_{1-4}$ alkanoyl protecting group to the corresponding $R_3$ $C_{1-4}$ alkyl group may be carried out directly by reduction under conventional conditions, for example with $LiAlH_4$ as the reducing agent in an inert solvent such as tetrahydrofuran.

Examples of group A' and B' convertible to A and B include alkylene chains containing a carbonyl group which may be reduced under conventional conditions with a suitable reducing agent such as LiAlH$_4$ in an inert solvent such as tetrahydrofuran.

Interconversion of groups R$_2$ may be carried out conventionally. Thus, for example, a group R$_2$ of the formula COR$_7$ may be reduced to the corresponding alkyl group CH$_2$R$_7$ under the conditions just described for the reduction of R$_3$' to R$_3$.

It will be appreciated that the selective removal or reduction of an R$_3$' protecting group will generally only be carried out in the presence of alkyl-type R$_2$ groups. Where R$_2$' and R$_3$' are both alkanoyl groups, similtaneous reduction of both moieties may be performed to give the corresponding R$_2$ and R$_3$ alkyl groups.

In the reaction between the compounds R$_{10}$X and R$_{11}$Y, the leaving group may be any suitable group as defined above for L, such as halo, particulary chloro or bromo, tosyloxy or mesyloxy and the nucleophilic substitution reaction carried out as described above for the reaction of compounds of formulae (IIIa) and (IV), preferably in an inert solvent such as xylene, toluene or trichloromethane at elevated temperature in the presence of a base such as triethylamine.

Suitable pairs of R$_{10}$X and R$_{11}$Y include:

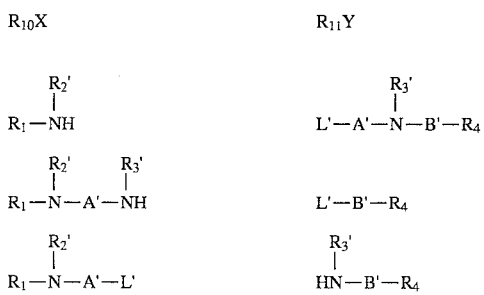

wherein L' is a leaving group and the remaining variables are as previously defined. The leaving group L' is a group readily displaceable by a nucleophile. Suitable examples for L' are as described above for L.

Where X or Y is an aldehyde or ketone function, the reaction is a reductive alkylation which may be carried out conventionally, for example in a solvent such as toluene or methanol with a reducing agent such as NaBH$_4$ or NaCNBH$_3$.

Suitable pairs of R$_{10}$X and R$_{11}$Y include:

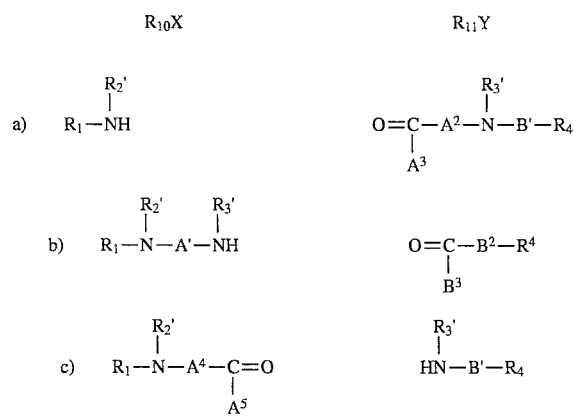

in which A', B', R$_1$, R$_2$', R$_3$' ana R$_4$ are as previously defined, a) provides a compound of formula (I) in which the alkylene motiety —A— is of the form

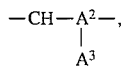

b) provides a moiety —B— of the form

and c) provides a moiety —A— of the form

Pharmaceutically acceptable salts including N-oxides of the compounds of formula (I) may be formed conventionally. The salts may be formed for example by reaction of the base compound of formula (I) with a pharmaceutically acceptable organic or inorganic acid.

N-oxides are produced by reaction of a compound of formula (I) with an organic peracid, such as m-chloroperbenzoic acid in, for example, a chlorinated hydrocarbon solvent at below ambient temperature.

Quaternary ammonium salts may be prepared by reaction of a compound of formula (I) with the appropriate alkyl, aryl or aralkyl, chloride, bromide or iodide. This reaction may be carried out in a solvent, such as acetone, methanol, ethanol or dimethyl formamide, at ambient or elevated temperature with or without pressure.

Racemates of compounds of the formula (I) may be resolved conventionally, e.g., by salification with a chiral acid if appropriate and separation of the resultant salts.

Alternatively, either may be synthesised from corresponding chiral preceeding intermediates.

The invention also provides novel intermediates of the formula (IIIa).

Compounds of formula (IIIa) may be prepared by any suitable conventional procedures, in particular nucleophilic substitution and/or reductive alkylation by analogy with the reaction of compounds R$_{10}$X and R$_{11}$Y described above.

Thus, for example, compounds of formula (IIIa) may be prepared by reacting the compound of formula (VII):

in which L$_1$ is a leaving group, A$^1$ is a group such that CH$_2$A$^1$ represents A, and R$_1$ is as above defined, with a compound of formula (VIII)

in which R$_3$" is R$_3$' or a group convertible thereto, and R$_4$ and B are as above defined, to give a compound of formula (IX):

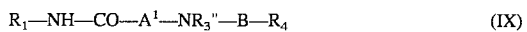

and thereafter reducing the compound of formula (IX) and, optionally or as necessary, converting R$_3$" to R$_3$'.

The leaving group L$_1$ is a group readily displaceable by a nucleophile. Suitable and preferred values for L$_1$ are described for L as hereinbefore defined. The reaction is carried out in an analogous manner to that between compounds of formulae (IIIa) and (IV), suitably in trichloromethane in the presence of triethylamine as the acid acceptor.

Where $R_3'$ in the compound of formula (III) is an alkanoyl function, suitable groups $R_3''$ convertible thereto include hydrogen, which may be converted to alkanoyl by reaction with the appropriate acid halide under conditions mentioned above for the reaction of the compounds of formulae (IIIa) and (IV) where L is halide, suitably in trichloromethane in the presence of triethylamine. Alternatively, when $R_3$ in formula (I) is an alkyl moiety, $R_3''$ may be the same alkyl moiety. The reduction of the compound of formula (IX) may be carried out under conventional amide reduction conditions as described above for the reduction of $R_3'$ to $R_3$, suitably with $LiAlH_4$ in tetrahydrofuran.

Compounds of the formula (IIIa) in which the alkylene moiety —A— is of the form $$-CHA^2- \atop | \atop A^3$$

may be prepared by the reductive alkylation of compound of formula (X)

$$R_1NH_2 \qquad (X)$$

in which $R_1$ is as above defined, with a compound of formula (XI):

$$R_4-B-NR_3''-A^2-\underset{A^3}{\overset{|}{C}}=O \qquad (XI)$$

where the variables are as above defined, followed by the optional conversion of $R_3''$ to $R_3'$ as described above.

The reductive alkylation may be carried out conventionally for example in a solvent such as toluene with a reducing agent such as $NaBH_4$.

Compounds of formula (IIIa) may alternatively be prepared by reacting a compound of formula (XII):

$$R_1-NH-A-NH_2 \qquad (XII)$$

wherein the variables are as above defined, with a compound of formula (XIII):

$$R_4BL_3 \qquad (XIII)$$

wherein $L_3$ is a leaving group and the remaining variables are as above defined, as described above for the nucleophilic substitution reaction of compounds $R_{10}X$ and $R_{11}Y$.

Examples of the leaving group $L_3$ include those described below for $L_2$.

Compounds $R_{10}X$ and $R_{11}Y$ are known compounds or may be prepared by processes analogous to those for preparing known compounds. Thus, for example, compound $R_{11}Y$ such as compounds of formula (XI) may be prepared by the reaction of a compound of formula (XIV):

$$\begin{matrix} O \\ \diagdown \\ \phantom{O}C-A^2-L_2 \\ \diagup | \\ O \phantom{C} A^3 \end{matrix} \qquad (XIV)$$

in which $L_2$ is a leaving group and $A^2$ and $A^3$ are as above defined, with a compound of formula (VIII) above, followed by deprotection of the protected carbonyl moiety under acid conditions. The reaction between the compounds of formulae (XIV) and (VIII) is preferably carried out in an inert solvent such as $CHCl_3$, with heating in the presence of a base such as triethylamine. Examples of the leaving group $L_2$ include halogen, tosylate, or other leaving groups described above for L.

Compounds $R_{11}Y$ of the form.

$$L'-A'-\underset{\phantom{N}}{\overset{R_3'}{\underset{|}{N}}}-B'-R_4$$

may be prepared as follows;

$$L'-A'-L_4 \quad + \quad HN-B'-R_4 \atop \phantom{L'-A'-L_4 \quad + \quad}{\overset{R_3'}{\underset{|}{\phantom{H}}}}$$

where $L_4$ is a leaving group such as described above for $L_3$ and the remaining variables are as previously described, under mildly basic conditions such as $K_2CO_3$ in an inert solvent such as dimethylformamide. Suitable examples of the groups L' and $L_4$ are chloro and bromo respectively.

Compounds $R_{10}X$ of the form:

$$R_1-\underset{\phantom{N}}{\overset{R_2'}{\underset{|}{N}}}-A'-\underset{\phantom{N}}{\overset{R_3'}{\underset{|}{N}}}H$$

may be prepared as follows:

$$R_1-\underset{\phantom{N}}{\overset{R_2'}{\underset{|}{N}}}-A'-L_5 \quad + \quad R_3'NH_2$$

where $L_5$ is a leaving group such as described for $L_4$ and the remaining variables are as previously descibed, in an inert solvent such as described above for the reaction of $R_{10}X$ and $R_{11}Y$.

Compounds $R_{10}X$ of the form:

$$R_1-\underset{\phantom{N}}{\overset{R_2'}{\underset{|}{N}}}-A^4-\underset{A^5}{\overset{|}{C}}=O$$

may be prepared as follows:

$$R_1-NH \quad + \quad L_6-A^4-\underset{A^5}{\overset{|}{C}}\!\!\begin{matrix} O \diagdown \\ \diagup \phantom{O} \\ \diagdown \phantom{O} \\ O \diagup \end{matrix}$$

where $L_6$ is a leaving group such as described above for $L_2$ and the remaining variables are as defined, in an inert solvent such as described above for the reaction for the reaction of $R_{10}X$ and $R_{11}Y$, in the presence of a base such as triethylamine at elevated temperature, followed by deprotection with acid.

Compounds $R_{10}X$ of the form:

$$R_1-\underset{\phantom{N}}{\overset{R_2'}{\underset{|}{N}}}-A-NH_2$$

such as compounds of formula (XII) may be prepared by the reaction of a compound of formula (XV)

$$\begin{matrix} A^8 \\ | \\ C=C-CN \\ | \phantom{=} | \\ A^7 \phantom{=} A^6 \end{matrix} \qquad (XV)$$

wherein each of $A^6$, $A^7$ and $A^8$ is hydrogen or alkyl such that $A^8$

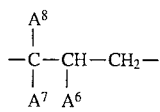

is A as above defined, with a compound of formula (XVI):

    (XVI)

followed by reduction of the resulting nitrile.

The reaction of the compounds of formulae (XV) and (XVI) is base catalysed, and the reduction step may be carried out using $LiAlH_4$.

The compounds of formulae (IV) to (VIII), (X) and (XIII) to (XVI), and analogous compounds $R_{10}X$ and $R_{11}Y$ are known compounds or may be prepared by processes analogous to those for preparing known compounds. Thus, compounds of formula (VII) may be prepared by reaction of the appropriately substituted aniline with a compound $L_1A^1COCl$ under the conditions mentioned above for the reaction of the compounds of formulae (IIIa) and (IV). Compounds of formula (VIII) may be prepared by the conventional amine alkylation or acylation of a compound $R_4BNH_2$ under similar conditions.

The invention therefore provides a process for the preparation of a compound of formula (IB) which process i comprises reacting together $R_{10}X$ and $YR_{11}$ as hereinbefore defined, to give a compound of formula (III) as defined, and thereafter, optionally or as necessary, converting $R_2'$, A', $R_3'$ and/or B' to $R_2$, A, $R_3$ and/or B, interconverting $R_2$ and/or $R_3$ and/or forming a pharmaceutically acceptable salt.

The following examples illustrate the invention and the following descriptions illustrate intermediates thereto.

Description 1 a) 3-(3,4-Dimethoxyphenyl)-1-chloro-propionamide (D1a)

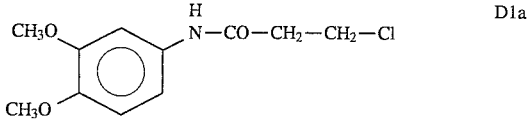

To a stirred dry solution of 85 g 3-chloropropionyl-chloride in 500 ml chloroform, a solution of 75 g 3,4-dimethoxyaniline and 54 g triethylamine in 200 ml chloroform was added dropwise with cooling at about 8°–10° C. The solution was then kept overnight at room temperature.

Thereafter, the solution was extracted with 1M NaOH and 0.5 icewater. The organic phase was neutralised, separated and dried over $Na_2SO_4$. The solvent was concentrated so that a white product was precipitated which was washed three times with ether.

The yield of the white crystalline product D1a was 60% and TLC-pure.

b) 2-(3,4-Dimethoxyphenyl)-1-chloro-acetamide (D1b)

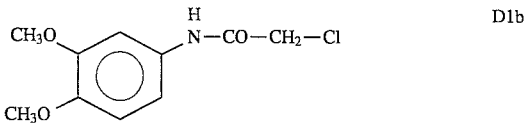

Compound D1b was prepared by the procedure of a) above, but using 2-chloroacetylchloride as the acylating agent.

Description 2 a) 1-[N-Methyl-N-2-(3,4-dimethoxyphenyl)-ethylamino]-3-propion-(3,4-dimethoxy)-anilide. (D2a)

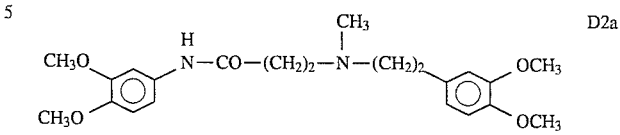

(i) N-Methoxycarbonyl-2-(3,4-dimethoxyphenyl)ethylamine

Equimolar amounts of 2-(3,4-dimethoxyphenyl)ethylamine, triethylamine and methyl chloroformate in dry tetrahydrofuran were mixed together carefully at around 20° C. After reaction overnight at room temperature, the solid was sucked off, the solvent evaporated and the residue extracted with small amounts of water in dichloromethane. After drying, the solvent was removed. The thus obtained product N-methoxycarbonyl-2-(3,4-dimethoxphenyl)-ethylamine in nearly quantitative yield is sufficiently pure for further reaction.

(ii) N-Methyl-2-(3,4-dimethoxyphenyl)-ethylamine

The product of (i) was reduced in dry tetrahydrofuran or diethylether in conventional manner by the addition of 3 equivalents of $LiAlH_4$ and subsequent refluxing of the mixture for 0.5–1 hr. After cooling and filtration, the solvent was evaporated and the product obtained by first extraction of the ethereal phase at pH 4, then at pH 10 with methylene chloride. Drying and evaporation of the solvent yielded 50–60% nearly pure oily product.

(iii) 1-[N-Methyl-N-2-(3,4-dimethoxyphenyl)-ethylamino]-3-propion-(3,4-dimethoxy)-anilide (title compound)

To a solution of 51 g 3-(3,4-Dimethoxyphenyl)-1-chloropropionamide (D1a) in 900 ml acetonitrile, 40 g N-methyl-2-(3,4-dimethoxyphenyl)-ethylamine from (ii) and 24 g triethylamine were added and the mixture refluxed for 7 h under moisture protection.

The solvent was removed in vacuo and the residue was extracted several times with ether at pH 6–7. Then the inorganic phase at PH 10 was extracted with methylenechloride, washed with water, dried over $Na_2SO_4$ and the organic solvent removed in vacuo.

Yield; 70 g yellow oil=65%.

The compound was sufficiently pure for further reaction.

b) 1-[N-methyl-N-2-(3,4-dimethoxyphenyl)-ethylamino]-2-acet-(3,4-dimethoxy)anilide. (D2b)

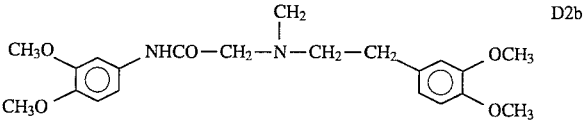

Compound D2b was prepared by the procedure of a) above but using intermediate D1b.

Description 3

1-[N-Methyl-N-2-(3,4-dimethoxyphenyl)-ethylamino]propyl-3-(3,4-dimethoxy)-aniline (D3)

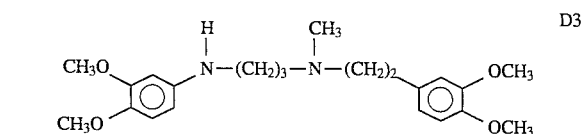

To a suspension of 6 g $LiAlH_4$ in 270 ml absolute tetrahydrofuran, a solution of 42 D2a in 240 ml THF was added dropwise under stirring, while the solvent was gently boiling.

The mixture was refluxed for 2 h, then stirred at room temperature for 1 h. Then excess LiAlH₄ and the complex formed was hydrolysed in the usual way by dropwise successive addition of 4.5 ml H₂O, 4.5 ml 15% NaOH and 14 ml water.

After stirring for 1 h, the white precipitate was sucked off, washed carefully with THF and the filtrate evaporated to dryness in vacuo.

The resulting dark green oil was extracted at pH 7–7.5 with excess ether. Then the aqueous phase at pH 12–13 was extracted with ether several times, and the extract washed with a small amount of water, dried over Na₂SO₄ and evaporated to dryness in vacuo.

32 g=80% of a dark green oil was obtained, sufficiently pure for further reaction.

The oil formed a crystalline grey-white hydrochloride when treated with ethanolic hydrochloride in refluxing absolute tetrahydrofuran. M.pt. 153° C.

Description 4

1-[N-Methyl-N-2-(3,4-dimethoxyphenyl)-ethylamino] ethyl-2-(3,4-dimethoxy)-aniline (D4)

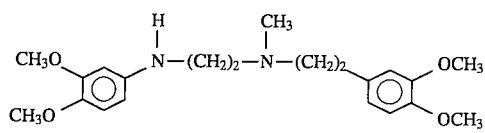

Compound D4 was prepared by the procedure of Description 3 but using intermediate D2b.

The following compounds of Descriptions 5 to 8 were prepared analogously to compound D3.

Description 5

1-[N-Methyl-N-2-(3,4-dimethoxyphenyl)ethylamino]propyl-3-aniline (D5)

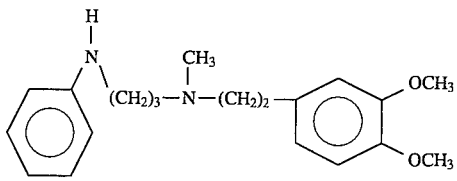

Description 6

1-[N-Methyl-N-2-phenylethylamino]propyl-3-(3,4-dimethoxy)-aniline (D6)

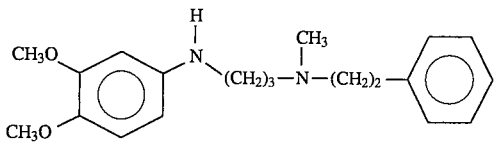

Description 7

1-[N-Methyl-N-2-phenylethylamino]propyl-3-aniline (D7)

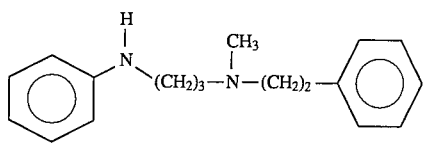

Description 8

1-[N-Methyl-N-2-(3,4-dimethoxyphenyl)ethylamino]propyl-3-(4-chloro)-aniline (D8)

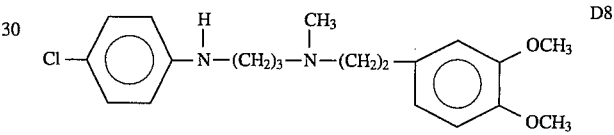

EXAMPLE 1

(N-[3,4-Dimethoxyphenyl]-N-3-[N'-2-(3,4-dimethoxyphenyl)phenyl)-ethyl-N'-methylamino]-propyl)-(2-nitro)benzylamine (E1)

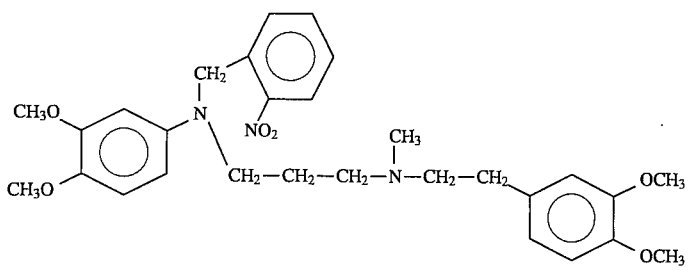

10 g 1-[N-Methyl-N-2-(3,4-dimethoxyphenyl)-ethylamino]propyl)-3-(3,4-dimethoxy)-aniline (D3), 3 g triethylamine and 5 g 2-nitrobenzyl-chloride in 100 ml chloroform were refluxed under protection from moisture for 8 h.

To complete the reaction, 0.7 g 2-nitrobenzylchloride and 0.5 g triethylamine were added and refluxed for another 2 h. Then the solvent was removed in vacuo and the residue extracted with ether several times at pH 6 and then extracted with dichloromethane twice at pH9.

After drying over Na₂SO₄, the CH₂Cl₂-phase was concentrated and the product purified by column-chromatography on Al₂O₃, using methylene chloride with 1–2% methanol as eluent.

Yield was 4 g of nearly pure material (red oil)≅31%.

In another bath, the raw material was purified using preparative TLC on silicagel with chloroform/methanol (9/1) as eluent. Yield was 22% of pure, red oily product.

Nmr: 1.55–2.0(m,2H): 2.29(s,3H); 2.35–2.8(m, 6H); (CDCl$_3$) 3.39(t(J=7.3 Hz),2H); 3.75(s,3H); 3.78(s,3H); 3.82(s,3H); 3.85(s,3H); 4.83(s,2H); 6.05–6.35 (m, 2H); 6.6–6.85(m, 4H); 7.3–7.6 (m, 3H); 8.0–8.2 (m, 1H)

EXAMPLE 2

(N-[3,4-Dimethoxyphenyl]-N-3-[N'-2-(3,4-dimethoxyphenyl)-ethyl-N'-methylamino]-propyl)-cyanamide (E2)

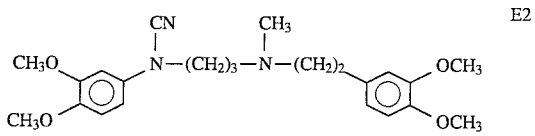

Compound E2 was prepared by reaction of 1 g amine D3 in 10 ml chloroform and 1 g K$_2$CO$_3$ with 0.32 g bromocyan (BrCN) at 0° C. Reaction was completed by stirring the mixture at room temperature for 1 h. After removing the solid by filtration and evaporation of the solvent in vacuo, the residue was purified by TLC-chromatography as described in Example 1.

Yield: 0.3 g≅30% of an red oily product.

| Elementary Analysis: | C | H | N |
|---|---|---|---|
| calc. | 66.80 | 7.55 | 10.16 |
| found | 66.74 | 7.49 | 10.14 |

EXAMPLE 3

(N-[3,4-Dimethoxyphenyl]-N-3-[N'-2-(3,4-dimethoxyphenyl)-ethyl-N'-methylamino]-propyl)-cyanomethylamine (E3)

Compound E3 was prepared from intermediate D3 and cyanomethylbromide by the procedure of Example 1.

| Elementary Analysis: | C | H | N |
|---|---|---|---|
| calc. | 67.42 | 7.78 | 9.83 |
| found | 67.35 | 7.66 | 9.78 |

The compounds of the following Examples 4 to 7 were prepared from intermediate D3 and the appropriately substituted benzylchloride by the procedure of Example 1:

EXAMPLE 4

(N-[3,4-Dimethoxyphenyl]-N-3-[N'-2-(3,4-dimethoxyphenyl)-ethyl-N'-methylamino]-propyl)-benzylamine (E4)

| Elementary Analysis: | C | H | N |
|---|---|---|---|
| calc. | 72.77 | 8.00 | 5.85 |
| found | 72.69 | 8.04 | 5.78 |

Nmr: 1.55–2.0(m,2H); 2.27(s,3H); 2.3–2.8(m, 6H); (CDCl$_3$) 3.36(t(J=7.3 Hz),2H); 3.74(s,3H); 3.78(s,3H); 3.84(s,6H); 4.44(s,2H); 6.1–6.45(m,2H); 6.6–6.9(m,4H); 7.1–7.4(m, 5H).

EXAMPLE 5

(N-[3,4-Dimethoxyphenyl]-N-3-[N'-2-(3,4-dimethoxyphenyl)-ethyl-N'-methylamino]-propyl)-(3-nitro)benzylamine (E5)

Nmr: 1.55–2.05(m, 2H); 2.28(s,3H); 2.3–2.8(m, 6H); (CDCl$_3$) 3.38(t(J=7.4 Hz),2H); 3.77(s,3H); 3.79(s,3H); 3.83–3.84(2xs, 6H); 4.49(s,2H); 6.1–6.4(m, 2H); 6.6–6.9(m, 4H); 7.3–7.7(m,2H); 7.95–8.2(m,2H).

EXAMPLE 6

(N-[3,4-Dimethoxyphenyl]-N-3-[N'-2-(3,4-dimethoxyphenyl)-ethyl-N'-methylamino]-propyl)-(4-nitro)-benzylamine (E6)

Nmr: 1.55–2.0(m, 2H); 2.28(s,3H); 2.3–2.8(m,6H); (CDCl$_3$) 3.37(t(J=7.5 Hz),2H); 3.76(s,3H); 3.78(s,3H); 3.83(s,3H); 3.84(s,3H); 4.5(s,2H); 6.1–6.4(m, 2H), 6.55–6.9(m,4H); 7.38(d(J=8.7 Hz),2H); 8.1(d(J=8.7 Hz), 2H).

EXAMPLE 7

(N-[3,4-Dimethoxyphenyl]-N-3-[N'-2-(3,4-dimethoxyphenyl)-ethyl-N'-methylamino]-propyl)-(4-methyl)benzylamine (E7)

Nmr: 1.5–2.0(m,2H); 2.28(s,3H); 2.31(s,3H); 2.35–2.8 (CDCl$_3$) (m,6H); 3.35(t(J=7.5 Hz),2H); 3.76(s,3H); 3.78(s, 3H); 3.84(s,6H); 4.41(s,2H); 6.15–6.45 (m, 2H); 6.55–6.85(m, 4H); 6.9–7.2(m,4H).

The compounds of the following Examples 8 and 9 were prepared from intermediate D4 and the appropriately substituted benzylchloride by the procedure of Example 1:

EXAMPLE 8

(N-[3,4-Dimethoxyphenyl]-N-2-N'-2-(3,4-dimethoxyphenyl)-ethyl-N'-methylamino]-ethyl)-benzylamine (E8)

Nmr: 2.34(s,3H); 2.5–2.8(m,6H); 3.49(t(J=7.7 Hz),2H), (CDCl$_3$) 3.74(s,3H); 3.79(s,3H); 3.84(s,6H); 4.47(s,2H); 6.1–6.45(m,2H); 6.6–6.9(m,4H); 7.1–7.4(m, 5H).

EXAMPLE 9

(N-[3,4-Dimethoxyphenyl]-N-2-[N'-2-(3,4-dimethoxyphenyl)-ethyl-N'-methylamino]-ethyl)-(3-nitro)benzylamine (E9)

Nmr: 2.33(s,3H); 2.45–2.8(m,6H); 3.48(t(J=7.2 Hz),2H); (CDCl$_3$) 3.76(s,3H); 3.79(s,3H); 3.84(s,6H); 4.51(s,2H); 6.1–6.4(m,2H), 6.55–6.9(m,4H); 7.3–7.7(m,2H); 8.0–8.2(m,2H).

The structure of the compounds of Examples 3 to 9 are illustrated in the following Table 1:

TABLE 1

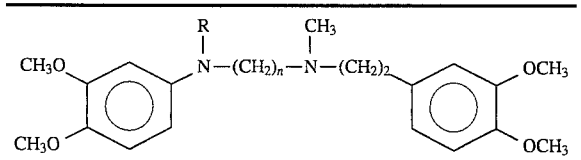

| Example No. | R | n |
|---|---|---|
| 3 | —CH$_2$CN | 3 |
| 4 | —CH$_2$—⌬ | 3 |

TABLE 1-continued

CH₃O—[Ar]—N(R)—(CH₂)ₙ—N(CH₃)—(CH₂)₂—[Ar]—OCH₃
(with CH₃O on left ring and OCH₃ on right ring)

| Example No. | R | n |
|---|---|---|
| 5 | CH₂—C₆H₄—NO₂ (para-nitrobenzyl) | 3 |
| 6 | CH₂—C₆H₄—NO₂ | 3 |
| 7 | CH₂—C₆H₄—CH₃ | 3 |
| 8 | CH₂—C₆H₅ | 2 |
| 9 | CH₂—C₆H₄—NO₂ | 2 |

EXAMPLE 10

(N-[3,4-dimethoxyphenyl]-N-3-[N'-2-(3,4-dimethoxyphenyl)-ethyl-N'-methylamino]-propyl)-butanoic acid amide (E10)

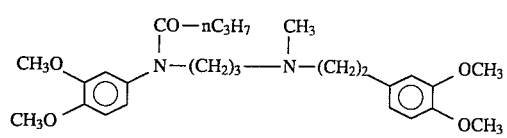

1 g Amine D3, 0.3 g triethylamine and 0.32 g butyric acidchloride in 40 ml dry chloroform was refluxed for 3 h. Isolation of the pure red oily product was achieved according to the procedure described in Example 1.

Yield 0.74 g≡65%

Nmr: 0.83(t(J=6.8 Hz),3H); 1.35–2.2(m,6H); 2.25(s,3H); (CDCl₃) 2.3–2.8(m,6H); 3.6–4.0(m+2s,14H); 6.6–7.0(m, 6H).

The compounds of the following Examples 11 to 19 were prepared from intermediate D3 and the appropriate acid chloride by the procedure of Example 10:

EXAMPLE 11

(N-[3,4-Dimethoxyphenyl]-N-3-[N'-2-(3,4-dimethoxyphenyl)-ethyl-N'-methylamino]-propyl)-(2-methyl)propanoic acid amide (E11)

| Elementary Analysis: | C | H | N |
|---|---|---|---|
| calc. | 68.10 | 8.35 | 6.11 |
| found | 68.12 | 8.42 | 5.91 |

Nmr: 1.02(d(J=6.7 Hz),6H); 1.5–1.95(m,2H); 2.26(s,3H); (CDCl₃) 2.3–2.8(m,7H); 3.5–4.0(m+2s,14H); 6.55–7.0 (m,6H).

EXAMPLE 12

(N-[3,4-Dimethoxyphenyl]-N-3-[N'-2-(3,4-dimethoxyphenyl)-ethyl-N'-methylamino]-propyl)-pentanoic acid amide (E12)

Nmr: 0.82(t(J=6.2 Hz),3H); 1.0–2.2(m,8H); 2.25(s,3H); (CDCl₃) 2.3–2.8(m,6H); 3.55–4.0(m+s,14H); 6.6–7.0(m, 6H).

EXAMPLE 13

(N-[3,4-Dimethoxyphenyl]-N-3-[N'-2-(3,4-dimethoxyphenyl)-ethyl-N'-methylamino]-propyl)-benzamide (E13)

| Elementary Analysis: | C | H | N |
|---|---|---|---|
| calc. | 70.71 | 7.36 | 5.68 |
| found | 70.60 | 7.38 | 5.64 |

EXAMPLE 14

(N-[3,4-Dimethoxyphenyl]-N-3-[N'-2-(3,4-dimethoxyphenyl)-ethyl-N'-methylamino]-propyl)-(2-phenyl)ethanoic acid amide (E14)

| Elementary Analysis: | C | H | N |
|---|---|---|---|
| calc. | 71.12 | 7.56 | 5.53 |
| found | 71.19 | 7.55 | 5.47 |

EXAMPLE 15

(N-[5,4-Dimethoxyphenyl]-N-3-[N'-2-(3,4-dimethoxyphenyl)-ethyl-N'-methylamino]-propyl)-(3-phenyl)propanoic acid amide (E15)

Nmr: 1.4–1.95(m,2H); 2.24(s,3H); 2.3–3.05(m,10H); (CDCl₃) 3.5–3.95(m+2s,14H); 6.4–6.9(m,6H); 7.0–7.4(m, 5H).

EXAMPLE 16

(N-[3,4-Dimethoxyphenyl]-N-3-[N'-2-(3,4-dimethoxyphenyl)-ethyl-N'-methylamino]-propyl)-(4-methyl)-phenyl sulphonamide (E16)

| Elementary Analysis | C | H | N |
|---|---|---|---|
| calc. | 64.18 | 7.05 | 5.16 |
| found | 64.09 | 7.02 | 5.15 |

EXAMPLE 17

(N-[3,4-Dimethoxyphenyl]-N-3-[N'-2-(3,4-dimethoxyphenyl)-ethyl-N'-methylamino]-propyl)-dodecanoic acid amide (E17)

Nmr: 0.87(t(J=5.2 Hz),3H); 1.0–2.2(m,22H); 2.26(s,3H); (CDCl₃) 2.3–2.8(m,6H); 3.6–4.0(m+2s,14H); 6.6–7.0(m, 6H).

EXAMPLE 18

(N-[3,4-Dimethoxyphenyl]-N-3-[N'-2-(3,4-dimethoxyphenyl)-ethyl-N'-methylamino]-propyl)-octanoic acid amide (E18)

Nmr: 0.84(t(J=7 Hz),3H); 1.0–2.2(m,14H); 2.25(s,3H); (CDCl₃) 2.3–2.8(m,6H); 3.5–4.0(m+2s,14H); 6.55–7.0(m, 6H).

EXAMPLE 19

(N-[3,4-Dimethoxyphenyl]-N-3-[N'-2-(3,4-dimethoxyphenyl)-ethyl-N'-methylamino]-propyl)-hexanoic acid amide (E19)

Nmr: 0.84(t(J=5.3 Hz),3H); 1.0–2.2(m,10H), 2.27(s,3H), (CDCl₃) 2.3–2.8(m,6H); 3.5–4.0(m+2s,14H); 6.6–7.0(m, 6H).

The compounds of the following Examples 20 to 23 were prepared from intermediate D4 and the appropriate acid chloride by the procedure of Example 10:

EXAMPLE 20

(N-[3,4-Dimethoxyphenyl]-N-2-[N'-2-(3,4-dimethoxyphenyl)-ethyl-N'-methylamino]-ethyl)-dodecanoic acid amide (E20)

Nmr: 0.87(t(J=6 Hz),3H); 1.0–1.8(m,18H); 1.8–2.15(m, 2H) (CDCl₃) 2.3(s,3H); 2.35–2.8(m,6H); 3.355–3.95 (m+3s, 14H); 6.55–6.95(m,6H).

EXAMPLE 21

(N-[3,4-Dimethoxyphenyl]-N-2-[N'-2-(3,4-dimethoxyphenyl)-ethyl-N'-methylamino]-ethyl)-pentanoic acid amide (E21)

Nmr: 0.82(t(J=6.2 Hz),3H); 0.95–1.8(m,4H); 1.9–2.2 (CDCl₃) (m,2H); 2.30(s,3H); 2.4–2.8(m,6H); 3.6–3.95 (m+3s,14H); 6.5–6.95(m,6H).

EXAMPLE 22

(N-[3,4-Dimethoxyphenyl]-N-2-[N'-2-(3,4-dimethoxyphenyl)-ethyl-N'-methylamino]-ethyl)-(2-methyl)propanoic acid amide (E22)

Nmr: 1.02(d(J=6.7 Hz),6H); 2.30(s,3H); 2.35–2.8(m,7H). (CDCl₃) 3.6–3.95(m+s, 14H); 6.65–6.95(m,6H).

EXAMPLE 23

(N-[3,4-Dimethoxyphenyl]-N-2-[N'-2-(3,4-dimethoxyphenyl)-ethyl-N'-methylamino]-ethyl)-(3-phenyl)propanoic acid amide (E23)

Nmr: 2.29(s,3H); 2.4–3.05(m,10H); 3.6–3.95(m+3s, 14H); (CDCl₃) 6.4–6.9(m,6H); 7.0–7.35(m,5H).

The structures of the compounds of Example 11 to 23 are illustrated in Table 1:

TABLE 1 (Contd.)

| Example No. | R | n |
|---|---|---|
| 11 | COi-C₃H₇ | 3 |
| 12 | COn-C₄H₉ | 3 |
| 13 | CO—C₆H₅ | 3 |
| 14 | COCH₂—C₆H₅ | 3 |
| 15 | CO(CH₂)₂—C₆H₅ | 3 |

TABLE 1 (Contd.)-continued

| Example No. | R | n |
|---|---|---|
| 16 | SO₂—C₆H₄—CH₃ | 3 |
| 17 | COnC₁₁H₂₃ | 3 |
| 18 | COnC₇H₁₅ | 3 |
| 19 | COnC₅H₁₁ | 3 |
| 20 | COC₁₁H₂₃ | 2 |
| 21 | COnC₄H₉ | 2 |
| 22 | COiC₃H₇ | 2 |
| 23 | CO(CH₂)₂—C₆H₅ | 2 |

EXAMPLE 24

(N-[3,4-Dimethoxyphenyl]-N-3-[N'-2-(3,4-dimethoxyphenyl)-ethyl-N'methylamino]-propyl)-n-butyl-urethane (E24)

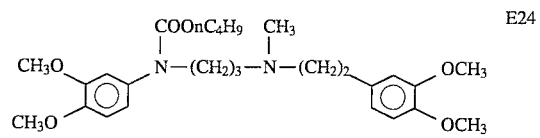

1 g Amine D3, 0.3 g triethylamine and 0.37 g n-butyl-chloro-formate in 20 ml chloroform were refluxed for 4 h. Isolation of the pure red oily product was achieved according to the procedure described in Example 1.

Yield: 0.9 g≅74%

| Elementary Analysis: | C | H | N |
|---|---|---|---|
| calc. | 66.37 | 8.25 | 5.73 |
| found | 66.47 | 8.25 | 5.76 |

EXAMPLE 25

(N-[3,4-Dimethoxyphenyl]-N-3-[N'-2-(3,4-dimethoxyphenyl)-ethyl-N'-methylamino]-propyl)-phenyl-urethane (E25)

Compound E25 was prepared from intermediate D3 and phenyl chloroformate by the procedure of Example 24.

| Elementary Analysis: | C | H | N |
|---|---|---|---|
| calc. | 68.48 | 7.13 | 5.50 |
| found | 68.58 | 7.22 | 5.39 |

EXAMPLE 26

(N-[3,4-Dimethoxyphenyl]-N-3-[N'-2-(3,4-dimethoxyphenyl)-ethyl-N'-methylamino]-propyl)-N''-n-butyl-urea (E26)

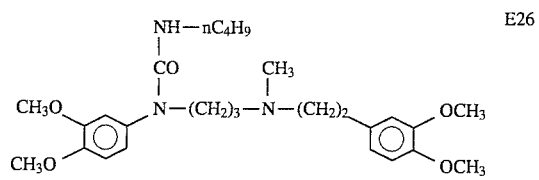

1 g Amine D3 and 0.28 g n-butylisocyanate in 25 ml chloroform were refluxed for 2 h.

After removing the solvent in vacuo, the pure product was isolated by TLC-chromatography as described in Example 1.

Yield: 0.9 g≅75% of an red, oily product

Nmr: 0.87(t(J=6.0 Hz),3H); 1.1–1.55(m,4H); (CDCl$_3$) 1.55–1.95(m,2H); 2.26(s,3H); 2.3–2.8(m,6H), 3.0–3.35(m, 2H); 3.5–3.95(m+2s(3.85, 3.89),14H); 4.34(t exch.D$_2$O, 1H); 6.55–7.0(m,6H).

The compounds of the following Examples 27 to 31 were prepared from intermediate D3 and the appropriate isocyanate by the procedure of Example 26:

EXAMPLE 27

(N-[3,4-Dimethoxyphenyl]-N-3-[N'-2-(3,4-dimethoxyphenyl)-ethyl-N'-methylamino]-propyl)-N''-n-propyl-urea (E27)

| Elementary Analysis: | C | H | N |
|---|---|---|---|
| calc. | 65.93 | 8.30 | 8.87 |
| found | 65.87 | 8.29 | 8.51 |

EXAMPLE 28

(N-[3,4-Dimethoxyphenyl]-N-3-[N'-2-(3,4-dimethoxyphenyl)-ethyl-N'-methylamino]-propyl)-N''-i-propyl-urea (E28)

| Elementary Analysis: | C | H | N |
|---|---|---|---|
| calc. | 65.93 | 8.30 | 8.87 |
| found | 65.98 | 8.23 | 8.82 |

EXAMPLE 29

(N-[3,4-Dimethoxyphenyl]-N-3-[N'-2-(3,4-dimethoxyphenyl)-ethyl-N'-methylamino]-propyl)-N''-t-butyl-urea (E29)

| Elementary Analysis: | C | H | N |
|---|---|---|---|
| calc. | 66.50 | 8.47 | 8.61 |
| found | 66.38 | 8.46 | 8.71 |

EXAMPLE 30

(N-[3,4-Dimethoxyphenyl]-N-3-[N'-2-(3,4-dimethoxyphenyl)-ethyl-N'-methylamino]-propyl)-N''-benzylurea (E30)

Nmr: 1.5–1.95(m,2H); 2.25(s,3H); 2.3–2.85(m,6H); (CDCl$_3$) 3.6–3.95(m+3s,14H); 4.41(d(J=5.8 Hz),exch.D$_2$O s,2H); 4.82(t(J=5.8 Hz)exch.D$_2$O,1H); 6.6–6.95 (m,6H); 7.1–7.45(m,5H).

EXAMPLE 31

(N-[3,4-Dimethoxyphenyl]-N-3-[N'-2-(3,4-dimethoxyphenyl)-ethyl-N'-methylamino3-propyl)-N''-phenylurea (E31)

| Elementary Analysis: | C | H | N |
|---|---|---|---|
| calc. | 68.61 | 7.34 | 8.27 |
| found | 68.28 | 7.28 | 7.94 |

The compounds of the following Examples 32 and 33 were prepared from intermediate D4 and the appropriate isocyanate by the procedure of Example 26:

EXAMPLE 32

(N-[3,4-Dimethoxyphenyl]-N-2-[N'-2-(3,4-dimethoxyphenyl)-ethyl-N'-methylamino]-ethyl-N''-(1-phenyl)-ethyl-urea (E32)

Nmr: 1.35(d(J=6.7 Hz),3H); 2.29(s,3H); 2.4–2.75 (CDCl$_3$) (m,6H); 3.6–3.95(m+3s,14H); 4.76(t(J=8 Hz), 1H exch.D$_2$O); 4.96(q(J=6.8 Hz),1H), 6.65–6.9(m,6H); 7.1–7.4(m,5H).

EXAMPLE 33

(N-[3,4-Dimethoxyphenyl]-N-2-[N'-2-(3,4-dimethoxyphenyl)-ethyl-N'-methylamino]-ethyl-N''-n-propyl-urea (E33)

Nmr: 0.82(t(J=6.8 Hz),3H); 1.1–1.6(m,2H), 2.32(s,3H), (CDCl$_3$) 2.45–2.8(m,6H); 2.9–3.3(m,exch.D$_2$O to 3.15, t(J= 5.84),2H); 3.65–3.95(m+2s,14H), 4.36(t(J=5 Hz) exch.D$_2$O, 1H); 6.55–6.95(m,6H).

The structures of the compounds of Examples 25 and 27 to 33 are illustrated in Table 1:

TABLE 1 (Cont.)

| Example No. | R | n |
|---|---|---|
| 25 | COO—⟨phenyl⟩ | 3 |
| 27 | CONHnC$_3$H$_7$ | 3 |
| 28 | CONHiC$_3$H$_7$ | 3 |
| 29 | CONH t-C$_4$H$_9$ | 3 |
| 30 | CONHCH$_2$—⟨phenyl⟩ | 3 |
| 31 | CONH—⟨phenyl⟩ | 3 |
| 32 | CONHCH*(CH$_3$)—⟨phenyl⟩ R-(+) | 2 |
| 33 | CONHnC$_3$H$_7$ | 2 |

EXAMPLE 34

(N-[3,4-Dimethoxyphenyl]-N-3-[N'-2-(3,4-dimethoxyphenyl)-ethyl-N'-methylamino]-propyl)-n-pentylamine (E34)

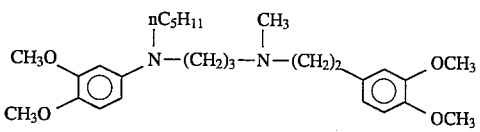

A mixture of 1.7 g E12 and 0.13 g LiAlH$_4$ in 16 ml dry tetrahydrofuran was refluxed under protection from moisture for 2 h. Thereafter, the product was worked up according to the procedure described for compound D3. Pure product was obtained by TLC as described for Example 1.

Yield: 0.24 g=15% of a oily red product

Nmr: 0.9(t(J=5.2 Hz),3H); 1.1–2.0(m,8H); 2.30(s,3H); (CDCl$_3$) 2.34–2.8(m,6H); 3.0–3.4(m,4H); 3.8(s,3H); 3.84(s, 9H), 6.1–6.45(m,2H), 6.6–6.95(m,4H).

Hydrochloride salt m.pt. 191° C. (prepared by treatment of the free base in ethyl acetate with ethanolic HCl. The salt crystallised on cooling and was washed with ether).

EXAMPLE 35

(N-[3,4-Dimethoxyphenyl]-N-2-[N'-2-(3,4-dimethoxyphenyl)-ethyl-N'-methylamino]ethyl)-n-pentylamine (E35).

The title compound was prepared from compound E21 by the procedure of Example 34.

Nmr: 0.91(t(J=6 Hz),3H); 1.1–1.8(m,6H); 2.38(s,3H); (CDCl$_3$) 2.4–2.85(m,6H); 3.05–3.5(m,4H), 3.81, 3.85, 3.86(s,s,s,12H); 6.1–6.4(m,2H); 6.55–6.9(m,4H).

The compounds of Examples 34 and 35 have also been prepared from compounds D3 and D4 respectively by the procedure of Example 1 but using n-pentyliodide in place of 2-nitrobenzyl chloride. Yield 20–35%.

The compound of Example 34 has also been prepared from compound D3 and valeraldehyde by the procedure of Example 61 at pH3. Yield 50–60%.

The compounds of the following Examples 36 to 46 were prepared from intermediate D3 (Examples 36 to 44) or D2 (Examples 45 and 46) by the procedure of Example 1. Example 37 utilized 3-(3-methoxyphenyl)-1-bromopropane. Example 44 utilized 2-chloro-3,5-dinitropyridine. The remaining examples utilised the appropriate alkyl chloride.

EXAMPLE 36

(N-[3,4-Dimethoxyphenyl]-N-3-[N'-2-(3,4-dimethoxyphenyl)-ethyl-N'-methylamino]-propyl)-3,5-dinitrobenzylamine Nmr: 1.55–2.0(m,2H); 2.29(s,3H); 2.3–2.9(m,6H), (CDCl$_3$) 3.2–3.55(m,2H), 3.78, 3.80, 3.83(3s,12H); 4.53(s, 2H); 6.1–6.5(m,2H); 6.6–6.9(m,4H); 8.35–8.5 (m,2H); 8.8–8.95(m,1H).

EXAMPLE 37

(N-[3,4-Dimethoxyphenyl]-N-3-[N'-2-(3,4-dimethoxyphenyl)-ethyl-N'-methylamino]-propyl)-3-(3-methoxy-phenyl)-propylamine nmr: 1.5–2.1(m,4H); 2.29(s,3H); 2.3–3.0(m,8H); (CDCl$_3$) 3.1–3.4(m,4H); 3.77, 3.79, 3.84, 3.85(4s,15H), 6.1–6.4(m,2H); 6.6–6.95(m,7H); 7.0–7.3(m,1H).

EXAMPLE 38

(N-[3,4-Dimethoxyphenyl]-N-3-[N'-2-(3,4-dimethoxyphenyl)-ethyl-N'-methylamino]-propyl)-2,5-dimethyl-benzylamine Nmr: 1.5–2.0(m,2H); 2.25, 2.28 (2s,9H); (CDCl$_3$) 2.3–2.9(m,6H); 3.2–3.55(m,2H); 3.76, 3.79,3.84, 3.85(4s, 12H); 4.34(s,2H); 6.1–6.4(m,2H); 6.6–7.2(m,7H)

EXAMPLE 39

(N-[3,4-Dimethoxyphenyl]-N-3-[N'-2-(3,4-dimethoxyphenyl)-ethyl-N'-methyl-amino]-propyl)-2-trifluoromethylbenzylamine Nmr: 1.5–2.1(m,2H); 2.29(s,3H); 2.3–2.8(m,6H), (CDCl$_3$) 3.25–3.6(m,2H); 3.7, 3.77, 3.82, 3.84(4s,12H); 4.67(s,2H); 6.05–6.3(m,2H); 6.6–6.9(m,4H); 7.25–7.5(m, 3H); 7.5–7.75(m,1H).

EXAMPLE 40

(N-[3,4-Dimethoxyphenyl]-N-3-[N'-2-(3,4-dimethoxyphenyl)-ethyl-N'-methyl-amino]-propyl)-3-trifluoromethylbenzylamine Nmr: 1.5–2.0(m,2H); 2.27(s,3H); 2.3–2.9(m,6H); (CDCl$_3$) 3.2–3.5(m,2H); 3.75, 3.79, 3.83, 3.84(4s,12H); 4.46(s,2H), 6.1–6.4(m,2H); 6.55–6.9 (m,4H); 7.3–7.65(m, 4H).

EXAMPLE 41

(N-[3,4-Dimethoxyphenyl]-N-3-[N'-2-(3,4-dimethoxyphenyl)-ethyl-N'-methyl-amino3-propyl)-2,4,6-trimethyl-benzylamine Nmr: 1.4–1.85(m,2H); 2.1–2.4(m+2s (2.19, 2.27), (CDCl$_3$) 14H); 2.4–3.2(m,6H); 3.76, 3.82, 3.84(3s, 12H);4.17(s,2H); 6.35–6.9(m,8H).

EXAMPLE 42

(N-[3,4-Dimethoxyphenyl]-N-3-[N'-2-(3,4-dimethoxyphenyl)-ethyl-N'-methyl-amino]-propyl)-2,6-dichlorobenzylamine Nmr: 1.4–1.9(m,2H), 2.21(s,3H), 2.25–2.28(m,6H), (CDCl$_3$) 3.0–3.3(m,2H); 3.81,3.84(2s,12H); 4.5(s,2H), 6.4–6.9(m,6H); 6.95–7.4(m,3H).

EXAMPLE 43

(N-[3,4-Dimethoxyphenyl]-N-3-[N'-2-(3,4-dimethoxyphenyl)-ethyl-N'-methyl-amino]-propyl)-2-chloro-3,4-methylenedioxobenzylamine Nmr: 1.55–2.0(m,2H); 2.3(s,3H); 2.35–2.9(m,6H), (CDCl$_3$) 3.2–3.55(m,2H); 3.77, 3.78, 3.83, 3.85(4s,12H); 4.41(s,2H); 5.90(s,2H), 6.05–6.35(m,2H); 6.6–6.9(m,6H).

EXAMPLE 44

(N-]3,4-Dimethoxyphenyl]-N-3-[N'-2-(3,4-dimethoxyphenyl)-ethyl-N'-methyl-amino]-propyl)-3,5-dinitro-2-aminopyridine Nmr: 1.5–2.1(m,2H); 2.26(s,3H); 2.3–2.8(m,6H); (CDCl$_3$) 3.82, 3.84, 3.86(3s,12H); 4.0–4.3(m,2H), 6.5–6.9(m,6H); 8.61(d(J=2.5 Hz),1H); 9.17(d(J=2.5 Hz), 1H).

EXAMPLE 45

(N-[3,4-Dimethoxyphenyl]-N-2-[N'-2-(3,4-dimethoxyphenyl)-ethyl-N'-methyl-amino]-ethyl)-4-nitro-benzyl-amine Nmr: 2.33(s,3H), 2.5–2.8(m,6H); 3.3–3.6(m,2H); (CDCl$_3$) 3.75, 3.79, 3.84(3s,12H); 4.52(s,2H); 6.05–6.4(m, 2H), 6.55–6.9(m,4H), 7.3–7.5(m,2H), 8.05–8.25(m,2H).

EXAMPLE 46

(N-[3,4-Dimethoxyphenyl]-N-2-[N'-2-(3,4-dimethoxyphenyl)-ethyl-N'-methylamino]-ethyl)benzylamine Nmr: 2.34(s,3H); 2.5–2.9(m,6H); 3.35–3.65(m,2H); (CDCl$_3$) 3.74, 3.79, 3.84(3s,12H); 4.47(s,2H); 6.1–6.45(m, 2H); 6.6–6.95(m,4H); 7.1–7.4(m,5H).

EXAMPLE 47

(N-[3,4-Dimethoxyphenyl]-N-2-[N'-2-(3,4-dimethoxyphenyl)-ethyl-N'-methyl-amino]-ethyl)phenylacetamide Nmr: 2.29(s,3H); 2.4–2.75(m,6H); 3.44(s,2H); (CDCl$_3$) 3.55–4.0(m+3s (3.69, 3.84, 3.90),14H); 6.5–7.5(m,11H).

The compounds of the following Examples 47 to 56 were prepared from amine D2 (Example 47) or D3(Example 48 to 56) and the appropriate acid chloride by the procedure of Example 10.

Example 56 utilized the acid chloride 3-phenyl-2-acetoxy-propanoic acid chloride prepared from L(−) phenyl lactic acid by conversion to the acetate by reaction with acetyl chloride in chloroform in the presence of triethylamine, followed by conversion to the acid chloride by treatment with thionyl chloride in chloroform.

EXAMPLE 48

(N-[3,4-Dimethoxyphenyl]-N-3-[N'-2-(3,4-dimethoxyphenyl)-ethyl-N'-methyl-amino]-propyl)-4-(4'-nitrophenyl)-butyramide Nmr: 1.5–2.2(m,6H); 2.25(s,3H); 2.3–3.0(m,8H), (CDCl$_3$) 3.55–3.8(m,2H); 3.84,3.85, 3.89(3s,12H); 6.5–6.95(m,6H); 7.25(d(J=8.8 Hz),2H), 8.09(d(J=8.8 Hz), 2H).

EXAMPLE 49

(N-[3,4-Dimethoxyphenyl]-N-3-[N'-2-(3,4-dimethoxyphenyl)-ethyl-N'-methylamino]-propyl)-(4-nitrophenyl)-acetamide Nmr: 1.5–1.95(m,2H); 2.25(s,3H); 2.3–2.95(m,6H); (CDCl$_3$) 3.53(s,2H); 3.6–3.75(m,2H); 3.79, 3.85, 3.92(3s, 12H); 6.45–7.0(m,6H), 7.25(d(J=8.7 Hz),2H); 8.09(d(J=8.7 Hz),2H).

EXAMPLE 50

(N-[3,4-Dimethoxyphenyl]-N-3-[N'-2-(3,4-dimethoxyphenyl)-ethyl-N'-methyl-amino]-propyl)-4-nitrobenzamide Nmr: 1.6–2.05(m,2H); 2.27(s,3H); 2.3–2.9(m,6H); (CDCl$_3$) 3.6–4.1(m+4s (3.73,3.81,3.85,3.86),14H); 6.4–6.9(m,6H); 7.44(d(J=8.9 Hz),2H); 8.03(d(J=8.9 Hz), 2H).

As the hydrochloride salt:
m.pt. 84° C.

| elementary analysis: | C | H | N | O | Cl |
|---|---|---|---|---|---|
| calc. | 60.67 | 6.32 | 7.32 | 19.51 | 6.18 |
| found: | 60.27 | 6.30 | 7.30 | 19.85 | 5.93 |

EXAMPLE 51

(N-[3,4-Dimethoxyphenyl]-N-3-[N'-2-(3,4-dimethoxyphenyl)-ethyl-N'-methyl-amino]-propyl)-n-heptanamide Nmr: 0.7–1.0(A(m),3H); 1.0–2.2(m,12H); 2.27(s,3H); (CDCl$_3$) 2.3–2.9(m,6H); 3.5–3.8(m,2H); 3.84, 3.86, 3.90(3s, 12H); 6.6–7.0(m,6H).

EXAMPLE 52

(N-[3,4-Dimethoxyphenyl]-N-3-[N'-2-(3,4-dimethoxyphenyl)-ethyl-N'-methylamino]-propyl)-4-cyanobenzamide hydrochloride m.pt. 86° C.

Nmr: 2.1–2.6(m,2H); 2.81(d(J=4 Hz), after D$_2$O (CDCl$_3$) exch.s, 3H); 2.95–3.5(m,6H); 3.8, 3.85, 3.99 (s,s,t(J=6 Hz), 14H); 6.4–7.0(m,6H); 7.3 –7.8(m,4H); 12.7(exch.D$_2$O,1H).

EXAMPLE 53

(N-[3,4-Dimethoxyphenyl]-N-3-[N'-2-(3,4-dimethoxyphenyl)-ethyl-N'-methyl-amino]-propyl)-4-trifluoromethylbenzamide hydrochloride m.pt. 67° C.

Nmr: 2.1–2.6(m,2H); 2.83(s,3H); 2.9–3.5(m,6H); (CDCl$_3$) 3.78, 3.81, 3.86, 4.01 (s,s,s,t(J=6.6 Hz),14H); 6.4–7.0(m,6H); 7.3–7.65(m,4H); 12.5 (D$_2$O exch.,1H).

EXAMPLE 54

(N-[3,4-Dimethoxyphenyl]-N-3-[N'-2-(3,4-dimethoxyphenyl)-ethyl-N'-methylamino]-propyl]-3,5-dinitrobenzamide hydrochloride m.pt. 128° C.

Nmr: 2.0–2.6(m,2H); 2.84(d(J=4.7 Hz) after D$_2$O exch. (CDCl$_3$) s,3H); 2.9–3.5(m,6H); 3.8, 3.87, 4.04 (s,s,t(J=6.5 Hz),14H); 6.6–7.0(m,6H); 8.53(d(J=1.7 Hz),2H); 8.89(d(J=1.7 Hz),1H); 12.7(exch.D$_2$O,1H).

EXAMPLE 55

(N-[3,4-Dimethoxyphenyl]-N-3-(N'-2-(3,4-dimethoxyphenyl)-ethyl-N'-methylamino]-propyl)-4-chlorobenzamide hydrochloride m.pt. solid foam Nmr: 2.1–2.6(m,2H); 2.8(s,3H); 2.9–3.4(m,6H); 3.79, (CDCl$_3$) 3.82, 3.85, 3.86 (4s+t(J=6.6 Hz),14H); 6.4–6.9(m, 6H); 7.0–7.4(m,4H); 12.5(exch.D$_2$O, 1H).

EXAMPLE 56

(N-[3,4-Dimethoxyphenyl]-N-3-[N'-2-(3,4-dimethoxyphenyl)-ethyl-N'-methyl-amino]-propyl)-(3-phenyl-2-acetoxy)-propanoic acid amide hydrochloride m.pt. 167° C.

Nmr: 2.0–2.6(m+s(2.25),5H); 2.82(d(J=4.3 Hz) after (CDCl$_3$) D$_2$O exch. s,3H); 3.0–3.6(m,6H); 3.6–4.3(m+ 4s(3.75, 3.81, 3.84, 3.86),17H); 6.5–7.35(m,11H); 12.5(exch. D$_2$O,1H).

EXAMPLE 57

(N-[3,4-Dimethoxyphenyl]-N-3-[N'-2-(3,4-dimethoxyphenyl)-ethyl-N'-methyl-amino]-propyl)-N"-4-nitrophenylurea The title compound was prepared from amine D3 and p-nitrophenylisocyanate by the procedure of Example 26.

Nmr: 1.55–2.0(m,2H); 2.32(s,3H); 2.35–2.9(m,6H); (CDCl$_3$) 3.6–4.0(m+3s (3.84, 3.88, 3.92),14H); 6.5–7.0(m, 6H); 7.45(d(J=9.2 Hz),2H); 7.55(m,1H, exch. with D$_2$O); 8.11(d(J=9.2 Hz),2H).

The compounds of the following Examples 58 to 60 were prepared from intermediate D3 and the appropriate alkylchloroformate by the procedure of Example 24.

EXAMPLE 58

(N-[3,4-Dimethoxyphenyl]-N-3-[N'-2-(3,4-dimethoxyphenyl)-ethyl-N'-methyl-amino]-propyl)-n-hexyl-urethane Nmr: 0.86(A,3H); 1.0–2.0(m,10H), 2.25(s,3H); (CDCl$_3$) 2.3–2.9(m,6H); 3.66(A(J=7 Hz),2H); 3.84, 3.85, 3.87 (3s, 12H); 4.07(A(J=6.3 Hz),2H); 6.5–6.95(m,6H).

EXAMPLE 59

(N-[3,4-Dimethoxyphenyl]-N-3-[N'-2-(3,4-dimethoxyphenyl)-ethyl-N'-methyl-amino]-propyl)-n-octyl-urethane Nmr: 0.87(m(A),3H); 1.1–2.0(m,14H); 2.25(s,3H); (CDCl₃) 2.3–2.9(m,6H); 3.5–3.8(m(A),2H), 3.84, 3.85, 3.87 (3s,12H); 3.95–4.2(m(A),2H); 6.5–6.95(m,6H).

EXAMPLE 60

(N-[3,4-Dimethoxyphenyl]-N-3-[N'-2-(3,4-dimethoxyphenyl)-ethyl-N'-methyl-amino]-propyl)-5-(–)-menthyl-urethane Nmr: 0.75–2.1(m,20H); 2.25(s,3H); 2.3–2.9(m,6H); (CDCl₃) 3.5–3.8(m,2H); 3.84, 3.85, 3.87 (3s,12H); 4.4–4.8(m,1H); 6.5–6.95(m,6H).

EXAMPLE 61

(N-[3,4-Dimethoxyphenyl]-N-3-[N'-2-(3,4-dimethoxyphenyl)-ethyl-N'-methyl-amino]-propyl)cyclohexyl-amine 1 g Amine (D3) was dissolved in 30 ml absolute methanol and ethanolic-HCl was added to pH 7. Then 0.3 g cyclohexanone, 0.5 g NaCNBH₃ and 3 Å molecular sieve was added and the mixture stirred for three days at room temperature.

For working up, the solid was filtered off, the filtrate evaporated to dryness and the residue at pH 12 extracted with methylene chloride. The extract was washed with water, dried over Na₂SO₄ and concentrated. The pure, oily product was isolated by TLC as described in Example 1.

Yield: 0.09 g≃7%

Nmr: 1.0–2.1(m,12H); 2.28(s,3H); 2.3–2.9(m,7H); (CDCl₃) 2.95–3.3(m,2H); 3.81, 3.84 (2s,12H); 6.2–6.5(m,2H); 6.6–6.95(m,4H).

The compounds of the following Examples 62 to 64 were prepared from amine D3 and the appropriate aldehyde or ketone by the procedure of Example 61.

EXAMPLE 62

(N-[3,4-Dimethoxyphenyl]-N-3-[N'-2-(3,4-dimethoxyphenyl)-ethyl-N'-methyl-amino]-propyl)-isopropylamine.

Nmr: 1.12(d(J=6.6 Hz), 6H); 1.5–1.9(m,2H); (CDCl₃) 2.28(s,3H); 2.3–3.25(m,8H); 3.6–3.9(m+3s(3.81,3.84,3.85), 13H); 6.2–6.5(m,2H); 6.6–6.85(m,4H).

EXAMPLE 63

(N-[3,4-Dimethoxyphenyl]-N-3-[N'-2-(3,4-dimethoxyphenyl)-ethyl-N'-methylamino]-propyl)-hexylamine Nmr: 0.89(A,3H); 1.1–2.0(m,10H); 2.3(s,3H); (CDCl₃) 2.35–2.9(m,6H); 3.0–3.4(m,4H); 3.80, 3.84, 3.85 (3s,12H); 6.1–6.45(m,2H); 6.6–7.0(m,4H).

EXAMPLE 64

(N-[3,4-Dimethoxyphenyl]-N-3-[N'-2-(3,4-dimethoxyphenyl)-ethyl-N'-methylamino]-propyl)-butylamine Nmr: 0.94(A(J=6 Hz),3H); 1.1–2.0(m,6H); 2.3(s,3H); (CDCl₃) 2.35–3.0(m,6H); 3.0–3.4(m,4H); 3.80(s,3H); 3.85(s,9H); 6.1–6.45(m,2H); 6.6–7.0(m,4H).

EXAMPLE 65

(N-[3,4-Dimethoxyphenyl]-N-3-[N'-2-(3,4-dimethoxyphenyl)-ethyl-N'-methylamino-propyl]-1-(3-oxo)butyramide The title compound was prepared by the reaction of amine D3 with 1.1 equivalents of diketene in methylene chloride at room temperature for 4 hours.

Nmr: 1.55–2.0(m,2H); 2.10(s,3H); 2.26(s,3H); (CDCl₃) 2.3–3.0(m,6H); 3.28(s,2H); 3.55–3.95(m+4s(3.84,3.86,3.89,3.90),14H); 6.55–7.0(m,6H).

The structures of the compounds of Examples 36 to 65 are illustrated in the following Table I:

TABLE 1 (contd)

| Example No. | R | n |
|---|---|---|
| 36 | CH₂–(C₆H₃)(NO₂)(NO₂) [2,4-dinitrobenzyl] | 3 |
| 37 | (CH₂)₃–(C₆H₄)–OCH₃ | 3 |
| 38 | CH₂–(C₆H₃)(CH₃)(CH₃) | 3 |
| 39 | CH₂–(C₆H₄)–CF₃ | 3 |
| 40 | CH₂–(C₆H₄)–CF₃ | 3 |
| 41 | CH₂–(C₆H₂)(CH₃)(CH₃)(CH₃) | 3 |
| 42 | CH₂–(C₆H₃)(Cl)(Cl) | 3 |
| 43 | CH₂–(C₆H₃)(O–CH₂–O) [methylenedioxybenzyl with Cl] | 3 |
| 44 | N–(C₆H₃)(NO₂)(NO₂) | 3 |

TABLE 1 (contd)-continued

| Example No. | R | n |
|---|---|---|
| 45 | CH₂—⌬—NO₂ (4-nitrobenzyl) | 2 |
| 46 | CH₂—⌬ (benzyl) | 2 |
| 47 | COCH₂—⌬ | 2 |
| 48 | CO(CH₂)₃—⌬—NO₂ | 3 |
| 49 | COCH₂—⌬—NO₂ | 3 |
| 50 | CO—⌬—NO₂ | 3 |
| 51 | CO<sub>n</sub>C₆H₁₃ | 3 |
| 52 | CO—⌬—CN | 3 |
| 53 | CO—⌬—CF₃ | 3 |
| 54 | CO—⌬(NO₂)(NO₂) (dinitro) | 3 |
| 55 | CO—⌬—Cl | 3 |
| 56 | CO—CH(OCOCH₃)—CH₂—⌬ | 3 |
| 57 | CONH—⌬—NO₂ | 3 |

TABLE 1 (contd)-continued

| Example No. | R | n |
|---|---|---|
| 58 | COO<sub>n</sub>C₆H₁₃ | 3 |
| 59 | COO<sub>n</sub>C₈H₁₇ | 3 |
| 60 | COO(−)-menthyl | 3 |
| 61 | cyclohexyl | 3 |
| 62 | iC₃H₇ | 3 |
| 63 | nC₆H₁₃ | 3 |
| 64 | nC₄H₉ | 3 |
| 65 | COCH₂COCH₃ | 3 |

The compounds of Examples 66 to 68 were prepared from the amine D5 and the corresponding alkyl chloride by the procedure of Example 1.

EXAMPLE 66

(N-phenyl-N-3-[N'-2-(3,4-dimethoxyphenyl)-ethyl-N'-methyl-amino]-propyl)-4-nitro-benzylamine.

Nmr: 1.55–2.05(m,2H); 2.29(s,3H); 2.3–2.9(m,6H); (CDCl₃) 3.46(A(J=7.2 Hz),2H); 3.82(s,3H); 3.84(s,3H), 4.59(s,2H); 6.5–6.95(m,6H); 7.0–7.5(m,4H); 8.15(d(J=8.7 Hz),2H).

EXAMPLE 67

(N-Phenyl-N-3-[N'-2-(3,4-dimethoxyphenyl)-ethyl-N'-methyl-amino]-propyl)-3-nitro-benzylamine.

Nmr: 1.55–2.05(m,2H); 2.29(s,3H); 2.30–2.9(m,6H); (CDCl₃) 3.48(A(J=7.2 Hz),2H); 3.82(s,3H); 3.84(s,3H); 4.59(s,2H); 6.5–6.9(m,6H); 7.05–7.6(m,4H); 7.95–8.2(m, 2H).

EXAMPLE 68

(N-Phenyl-N-3-[N'-2-(3,4-dimethoxyphenyl)-ethyl-N'-methyl-amino]-propyl)-2-nitro-benzylamine.

Nmr: 1.55–2.0(m,2H); 2.30(s,3H); 2.35–2.9(m,6H); (CDCl₃) 3.45(A(J=7.2 Hz),2H); 3.82(s,3H); 3.84(s,3H); 4.93(s,2H); 6.4–6.9(m,6H); 7.0–7.6(m,5H); 8.0–8.3(m,1H).

EXAMPLE 69

(N-Phenyl-N-3-[N'-2-(3,4-dimethoxyphenyl)-ethyl-N'-methyl-amino]-propyl)-valeramide Nmr: 0.8(A(J=6.2 Hz),3H); 0.95–2.2(m,8H); (CDCl₃) 2.24(s,3H);2.3–2.9(m,6H); 3.55–3.8(m,2H); 3.84(s,3H); 3.85(s,3H); 6.55–6.95(m,3H); 7.0–7.6(m,5H).

The title compound was prepared from amine D5 and pentanoic acid chloride by the procedure of Example 10.

The structures of the compounds of Examples 66 to 69 are illustrated in the following Table 2,

TABLE 2

| Example No. | R | n |
|---|---|---|
| 66 | 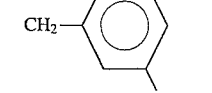 | 3 |
| 67 | 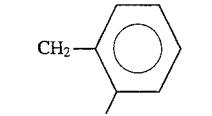 | 3 |
| 68 | 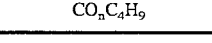 | 3 |
| 69 | $CO_nC_4H_9$ | 3 |

The following compounds of Examples 70 to 73 were prepared from the amine D6 and the corresponding alkyl chloride by the procedure of Example 1.

EXAMPLE 70

(N-[3,4-Dimethoxyphenyl]-N-3-[N'-(2-phenyl-ethyl)-N'-methylamino]-propyl)-benzylamine.

Nmr: 1.55–2.0(m,2H); 2.28(s,3H); 2.3–2.9(m,6H), (CDCl$_3$) 3.35(A(J=7 Hz),2H); 3.74(s,3H); 3.78(s,3H); 4.44(s,2H); 6.1–6.45(m,2H); 7.74(d(J=8.5 Hz), 1H); 7.0–7.5(m,10H).

EXAMPLE 71

(N-[3,4-Dimethoxyphenyl]-N-3-[N'-(2-phenyl-ethyl)-N'-methylamino]-propyl)-2-nitrobenzylamine Nmr: 1.55–2.05(m,2H); 2.30(s,3H); 2.35–2.9(m,6H); (CDCl$_3$) 3.34(A(J=7.2 Hz),2H); 3.74(s,3H); 3.78(s,3H); 4.80(s,2H); 6.05–6.4(m,2H); 6–72(d(J=8.6 Hz), 1H); 7.05–7.7(m,8H); 7.95–8.15(m,1H).

EXAMPLE 72

(N-[3,4-Dimethoxyphenyl]-N-3-[N'-(2-phenyl-ethyl)-N'-methylamino]-propyl)-3-nitrobenzylamine Nmr: 1.6–2.0(m,2H); 2.28(s,3H); 2.3–2.95(m,6H); (CDCl$_3$) 3.35(A(J=7.4 Hz),2H); 3.76(s,3H); 3.78(s,3H); 4.48(s,2H); 6.1–6.4(m,2H); 6.72(d(J=8.6 Hz), 1H); 7.0–7.65(m,7H); 7.9–8.2(m,1H).

EXAMPLE 73

(N-[3,4-Dimethoxyphenyl]-N-3-[N'-(2-phenyl-ethyl)-N'-methyl-amino]-propyl)-4-nitrobenzylamine Nmr: 1.5–2.0(m 2H); 2.29(s,3H); 2.3–2.95(m,6H); (CDCl$_3$) 3.2–3.5(m,2H); 3.75(s,3H); 3.78(s,3H); 4.50(s, 2H); 6.05–6.4(m,2H); 6.73(d(J=8.8 Hz),1H); 7.0–7.5(m, 7H); 8.14(d(J=8.6 Hz),2H).

EXAMPLE 74

(N-[3,4-Dimethoxyphenyl]-N-3-[N'-(2-phenyl-ethyl)-N'-methyl-amino]-propyl)-valeramide The title compound was prepared from amine D6 and pentanoic acid chloride by the procedure of Example 10.

Nmr: 0.82(A(J=6.2 Hz),3H); 0.95–2.2(m,8H); (CDCl$_3$) 2.28(s,3H); 2.3–2.95(m,6H); 3.69(A(J=7.3 Hz),2H); 3.86(s, 3H); 3.90(s,3H); 6.55–6.95(m,3H); 7.0–7.5(m,5H).

The structures of the compounds of Examples 70 to 74 are illustrated in the following Table 3:

TABLE 3

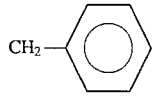

| Example No. | R | n |
|---|---|---|
| 70 | 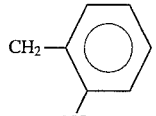 | 3 |
| 71 | 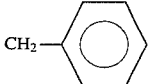 | 3 |
| 72 | 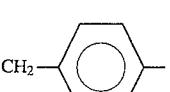 | 3 |
| 73 |  | 3 |
| 74 | $CO_nC_4H_9$ | 3 |

The following compounds of Examples 75 to 77 were prepared from amine D7 and the corresponding alkyl chloride by the procedure of Example 1.

EXAMPLE 75

(N-Phenyl-N-3-[N'-(2-phenyl-ethyl)-N'-methyl-amino]propyl)-3-nitrobenzylamine

Nmr: 0.55–2.0(m,2H); 2.29(s,3H); 2.3–2.9(m,6H), (CDCl$_3$) 3.3–3.6(m,2H); 4.56(s,2H); 6.5–6.9(m,3H), 7.0–7.35(m,7H); 7.4–7.65(m,2H); 7.9–8.3(m,2H).

EXAMPLE 76

(N-Phenyl-N-3-[N'-(2-phenyl-ethyl)-N'-methyl-amino]propyl)-4-nitrobenzylamine

Nmr: 1.55–2.0(m,2H); 2.29(s,3H); 2.3–3.0(m,6H), (CDCl$_3$) 3.3–3.6(m,2H); 4.57(s,2H); 6.5–6.9(m,3H); 7.0–7.5(m,9H), 8.14(d(J=8.6 Hz),2H).

EXAMPLE 77

(N-Phenyl-N-3-[N'-(2-phenyl-ethyl)-N'-methyl-amino]propyl)-2-nitrobenzylamine

Nmr: 1.55–2.05(m,2H); 2.30(s,3H); 2.35–3.0(m,6H); (CDCl₃) 3.3–3.6(m,2H); 4.90(s,2H); 6.4–6.8(m,3H); 7.0–7.6(m,10H); 8.0–8.3(m,1H).

EXAMPLE 78

(N-Phenyl-N-3-[N'-(2-phenyl-ethyl)-N'-methyl-amino]propyl)-valeramide

The title compound was prepared from amine D7 and pentanoic acid chloride by the procedure of Example 10.

Nmr: 0.80(A(J=6.2 Hz),3H); 0.95–2.2(m,8H); (CDCl₃) 2.24(s,3H); 2.3–2.9(m,6H); 3.72(A(J=7.3 Hz),2H), 7.0–7.6(m,10H).

The structures of the compounds of Examples 75 to 78 are illustrated in the following Table 4:

TABLE 4

Structure: Ph–N(R)–(CH₂)ₙ–N(CH₃)–(CH₂)₂–Ph

| Example No. | R | n |
|---|---|---|
| 75 | CH₂–(phenyl with NO₂ ortho) | 3 |
| 76 | CH₂–(phenyl with NO₂ para) | 3 |
| 77 | CH₂–(phenyl with NO₂ meta) | 3 |
| 78 | CO₂C₄H₉ | 3 |

EXAMPLE 79

(N-(4-Chloro)phenyl-N-3-[N'-2-(3,4-dimethoxy-phenyl-)ethyl-N'-methyl-amino]-propyl)-4-nitrobenzamide hydrochloride

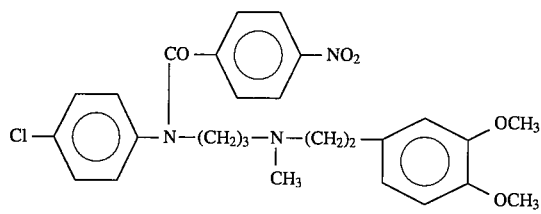

The title compound was prepared from amine D8 and 4-nitrobenzoyl chloride by the procedure of example 10. m.pt. 115° C.

Nmr: 2.1–2.6(m,2H); 2.83(d(J=4.5 Hz) exch.D₂O s,3H); (CDCl₃) 2.95–3.5(m,6H); 3.85, 3.87, 4.02 (2s+t (J=6.5 Hz), 8H); 6.6–6.9(m,3H); 6.95–7.6(m,6H); 7.9–8.2(m,2H); 12.6 exch.D₂Os,1H).

The compounds of Examples 1 to 51 and 57 to 78 are all oils in their free base form.

PHARMACOLOGICAL DATA

1. Coronary Vasodilating activity
   a) Vasopressin test in anaesthetized rats
   Vasopressin (Lysopressin: 1 I.U./kg) was administered intravenously in order to provoke coronary spasm (ST-segment elevation in the ECG). Compound E1 was active against coronary spasm at a dose of 0.6 g/kg i.d.

The ability of test compounds to reduce coronary spasm is taken as a measure of their anti-anginal potential in spasm-induced angina pectoris. (Ref. Drug. Res. 33(11), 8,1117–1121 (1983)).

b) Pig isolated coronary artery
   Coronary artery spirals were prepared and in lengths from 1.5 to 2 cm were incubated at 32.5° in $Ca^{++}$-free Krebs-Henseleit solution containing tris Duffer and 60 mM KCl. $Ca^{++}$ in concentrations ranging from 0.1 mM-7 mM was given every 10 min to produce a control dose-response curve. Following a wash out circle using EDTA, either placebo or drug was administered, and an equilibration time of 30 minutes allowed before the second dose-response curve was made. Dose-ratios were calculated at $ED_{50}$-levels, from these the log $K_B$ was calculated. Compound E4 showed a log $K_B$ of 5.85, which indicates moderate to medium $Ca^{++}$-antagonistic activity in coronary artery in vitro.

2. Haemodynamic profile in anaesthetized rats.

The effect of compounds of the invention on heart rate, systolic left ventricular pressure, left ventricular dp/dt max and mean arterial blood pressure was investigated so as to obtain information on the anti-anginal potential of these compounds, by reducing the oxygen demand of the ischaemic heart. Results are shown in Table 5.

TABLE 5

| Compound Number | haemodynamic effects (rat) $D_{hr}^{20}$* | % effect of $D_{hr}^{20}$ on LVP** | BP*** | $dp/dt_{max}$ | i.v. duration of action on heart rate (rat) (min) |
|---|---|---|---|---|---|
| E1  | 1.6 | −2  | 0   | −3  | 10 |
| E4  | 3.2 | −3  | −6  | −12 | 10 |
| E6  | 0.4 | +5  | +1  | −5  | 60 |
| E12 | 1.6 | −6  | −11 | −6  | 10 |
| E15 | 1.6 | −7  | −8  | −7  | 10 |
| E24 | 3.2 | −13 | −15 | −8  | 10 |
| E25 | 0.8 | −10 | −14 | −2  | 10 |
| E27 | 6.4 | −2  | −4  | −1  | 5–10 |
| E30 | 1.6 | −10 | −15 | −20 | 10 |
| E32 | 3.2 | −7  | −13 | −3  | 10 |
| E34 | 1.6 | −9  | −9  | −10 | 5–10 |
| E44 | 3.2 | −6  | −10 | −8  | 10 |
| E50 | 1.6 | −1  | −1  | −5  | 10 |
| ᵃ(E50 | 16 | — | −6 | — | >90) |

*$D_{hr}^{20}$ = i.v. dose which reduces heart rate by ca. 20%
**LVP = systolic left ventricular pressure
***BP = mean arterial blood pressure
ᵃ = i.d. administration Results The above results demonstrate that the compounds of the invention have therapeutic potential in both stable and variant angina pectoris. Of special interest is the bradycardic activity without marked hypotension of the test compounds.

Toxicity

No toxic effects were observed in the above of the tests.

I claim:

1. A compound of formula (IIa):

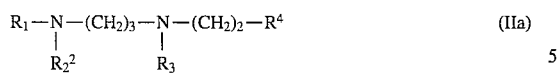

wherein $R_1$ and $R_4$ each represent 3,4 dimethoxyphenyl; $R_2^2$ is $CO_2R^7$ wherein $R_7$ is phenyl, 2-, 3- and 4-nitrophenyl, 3,5-dinitrophenyl, 3-methoxyphenyl, 3-methoxy-6-methylphenyl, 2-trifluoromethylphenyl, 2,4,6-trimethylphenyl, 2,6-dichlorophenyl, 4-cyanophenyl, 4-chlorophenyl and 4-methylphenyl; and $R_3$ is hydrogen.

2. A pharmaceutical composition comprising the compounds of formula IIa as defined in claim 1 and a pharmaceutical acceptable carrier.

3. A method of treatment or prophylaxis of angina in mammals, such as humans, which comprises the administration to a mammal in need thereof an effective amount of a compound of formula IIa as described in claim 1.

* * * * *